United States Patent
Goldman et al.

(10) Patent No.: US 6,833,447 B1
(45) Date of Patent: Dec. 21, 2004

(54) MYXOCOCCUS XANTHUS GENOME SEQUENCES AND USES THEREOF

(75) Inventors: Barry S. Goldman, Acton, MA (US); Gregory J. Hinkle, Plymouth, MA (US); Steven C. Slater, Acton, MA (US); Roger C. Wiegand, Wayland, MA (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 09/902,540

(22) Filed: Jul. 10, 2001

Related U.S. Application Data

(60) Provisional application No. 60/217,883, filed on Jul. 10, 2000.

(51) Int. Cl.[7] .............................................. C07H 21/00
(52) U.S. Cl. ...................... 536/23.1; 435/252.3; 800/13
(58) Field of Search ............................ 536/23.1, 24.32; 435/252.3; 800/13

(56) References Cited

PUBLICATIONS

Darwin et al., Regulation and sequence of the structural gene for cytochrome c552 from *Escherichia coli*: not a hexahaem but a 50kDa tetrahaem nitrite reductase. 1993, Molecular Microbiology, vol. 9, No. 6, pp. 1255–1265.*

* cited by examiner

*Primary Examiner*—Ardin H. Marschel
*Assistant Examiner*—Carolyn L. Smith
(74) *Attorney, Agent, or Firm*—Donna E. Scherer; Thomas E. Kelley; Lawrence M. Lavin, Jr.

(57) ABSTRACT

The present invention relates to nucleic acid sequences from the bacterium, *Myxococcus xanthus* and, in particular, to genomic DNA sequences. The invention encompasses nucleic acid molecules present in non-coding regions as well as nucleic acid molecules that encode proteins and fragments of proteins. In addition, proteins and fragments of proteins so encoded and antibodies capable of binding the proteins are encompassed by the present invention. The invention also encompasses oligonucleotides including primers, e.g. useful for amplifying nucleic acid molecules, and collections of nucleic acid molecules and oligonucleotides, e.g. in microarrays. The invention also provides constructs and transgenic cells and organisms comprising nucleic acid molecules of the invention. The invention also relates to methods of using the disclosed nucleic acid molecules, oligonucleotides, proteins, fragments of proteins, and antibodies, for example, for gene identification and analysis, and preparation of constructs and transgenic cells and organisms.

5 Claims, No Drawings

MYXOCOCCUS XANTHUS GENOME SEQUENCES AND USES THEREOF

CROSS-REFERENCE TO RELATED APPLICATION

This application claims priority under 35 U.S.C. §119(e) of U.S. Provisional Application No. 60/217,883 filed Jul. 10, 2000, the disclosure of which application is incorporated herein by reference in its entirety.

INCORPORATION OF SEQUENCE LISTING

Two copies of the sequence listing (Copy 1 and Copy 2) and a computer readable form of the sequence listing, all on CD-ROMs, each containing the file named Pa_00359.rpt which is 39,705,377 bytes (measured in MS-WINDOWS) and was created on Jun. 12, 2001 are herein incorporated by reference.

INCORPORATION OF TABLES 1, 2 AND 3

Two copies of Table 1 on CD-ROMs, each containing 998,830 bytes (measured in MS-WINDOWS) and all having the file name pa_00359.txt Table all created on Jun. 12, 2001, are herein incorporated by reference.

FIELD OF THE INVENTION

Included in the disclosure are nucleic acid molecules representing the, genome of the bacterium *Myxococcus xanthus* and, in particular, to nucleic acid molecules having nucleic acid sequences corresponding to DNA replication elements, genes, promoters, and other regulatory elements found in the *M. xanthus* genome. Also disclosed are homologous nucleic acid molecules, complementary nucleic acid molecules, polypeptides expressed by *M. xanthus* gene sequences, constructs comprising *M. xanthus* promoters, regulatory elements and/or genes, transformed cells and organisms comprising *M. xanihus* promoters, regulatory elements and/or genes, primers useful for replicating all or portions of *M. xanthus* genes or other *M. xanthus* nucleic acid molecules, computer readable media comprising sets of *M. xanthus* nucleic acid sequences, polypeptides and oligonucleotides, collections of *M. xanthus* nucleic acid molecules and methods of using such molecules and sequences including the use of collections of nucleic acid molecules in gene identification and gene expression analysis, development of a stoichiometric metabolic model, and preparation of constructs.

BACKGROUND OF THE INVENTION

*Myxococcus xanthus* is a Gram-negative, rod-shaped bacterium with gliding motility that is classified within the delta subgroup of bacteria. It is a member of a group of microorganisms, commonly called myxobacteria, that generally survive by degrading organic material and other organisms in the soil. Of particular interest within the myxobacteria is the social behavior among cells. Myxobacteria form social interactions that facilitate feeding and, when nutrients become scarce, sporulation. They are the only bacteria that practice both types of social behavior, and the mechanism of communication among cells has been the subject of much research (see *Myxobacteria II*. 1993. Martin Dworkin and Dale Kaiser (ed.), American Society for Microbiology, Washington, D.C.). *M. xanthus* has been particularly well studied, and is the member of the myxobacteria with the firmest genetic and physical map on which to build a genome project. An ordered YAC library and physical map of the *M. xanthus* genome have been constructed (He et al., *Proc Natl Acad Sci USA*. 91:9584–9587 (1994); Kuspa et al., *Proc Natl Acad Sci U S* 91:8917–8921 (1989)). The circular genome has been estimated to be around 9.5 Mbp (Shimkets, "The Myxobacterial Genome," in *Myxobacteria II. American Society for Microbiology*, Dworkin and Kaiser (eds.), Washington, D.C., pp. 85–107 (1993)), which is quite large for a bacterial genome. It also has a very high G+C content (around 70%: Kaiser et al., *Ann. Rev. Microbiol.* 33:595–639 (1979)) which makes sequencing and assembly of the genome a significant technical challenge.

Ecology and Life Cycle of *M. xanthus*

Myxobacteria are predatory organisms that can attack and degrade many other types of bacteria. Whole colonies of myxobacteria generally migrate together (swarm), and the combined production of extracellular enzymes allows more efficient solubilization of nutrients. Motility is accomplished by gliding, but the mechanism of gliding motility is not understood, either for myxobacteria or other types of gliding bacteria. The cells continue to feed communally until nutrients have been exhausted. Once nutrients become limiting, myxobacteria initiate a complex developmental process that leads to the production of fruiting bodies containing myxospores. Myxospores are resistant to heat, desiccation and other environmental insults, and serve as the resting phase for myxobacteria. The myxospores remain dormant until nutrients are again available, at which point they germinate to produce a new swarm of motile cells.

The sporulation process requires aggregation of many cells to an area where the fruiting body will eventually form. Both aggregation and fruiting body formation require a complex set of cell-to-cell communication networks, and a series of genetic switches within individual cells. The genetic cascade leads to differentiation of certain cells within the fruiting body, thereby producing myxospores.

The cells initially form a small, translucent mound. A portion of the cells within the mound begin to develop into myxospores, and the fruiting body eventually becomes about 0.1 mM high and dark as the thick spore walls are formed. The spores allow *M. xanthus* to survive harsh conditions for a long period of time, thus allowing the cells to be safely transported to a new location, perhaps by wind or within the gut of an animal.

Genetic analyses have identified a series of Myxococcus regulatory mutants that are defective in fruiting body formation. These mutants terminate at various points along the developmental pathway, and have defined four different chemical signaling factors, designated A, B, C, and D, that are required for normal sporulation (Kroos et al., *Genes and Development* 1:840–854 (1987); Losick et al., *Scientific American*. 276:68–73 (1997); Lee et al., *J. Bacteriol*. 178:977–984 (1996); Munoz et al., *Microbiologia Madrid*. 11:429–438 (1995); Kim, *Trends in Genetics*. 7:361–365 (1991)). Factors A and C are the best studied. A-factor is required for aggregation of the cells. It is actually a combination of factors, including a heat stable component that appears to be a complex mixture of amino acids (Kuspa et al., *J. Bacteriol*. 174:3319–3326 (1992)) and a heat labile portion that includes a mixture of peptidases that presumably generate amino acids (Plamann et al., *J. Bacteriol*. 174:3311–3318 (1992)). A-factor is diffusible, and therefore does not require direct cell-to-cell contact for signal transmission. In contrast, C-Factor is normally found tightly associated with the cell surface of the signal producer, and transmission requires close contact between the signal producer and the recipient. Thus, C-signaling requires cellular motion and the close physical contact of the swarming cells in an aggregate. Both signal types provide the necessary format for the required message; A-factor to attract distant cells to a focus, and C-factor to maintain communication within the developing fruiting body. Each of the signals leads to a cascade of genetic switches that continues the cell differentiation process.

Many of the downstream regulatory and effecter genes have now been identified in *M. xanthus* using genetic and biochemical approaches, and it is the speed and efficiency with which bacteria allow analysis of the complex networks and metabolic pathways that provides a primary utility of the genome sequence.

The nucleic acid molecules and sequences disclosed herein represent a substantial portion of the *M. xanthus* genome. These molecules and sequences may be used to identify novel genes, for example genes involved in antibiotic production, and sequences in regulatory regions of the *Myxococcus* genes provided herein. The *M. xanthus* molecules and sequences also permit identification of genetic sequences from other organisms, including plants, mammals such as humans, bacteria, other filamentous fungi and non-filamentous fungi such as a yeast, e.g. by comparison of such sequences with *M. xanthus* sequences. The availability of a substantially complete set of genes or partial genes of the *M. xanthus* genome permits the definition of primers for fabricating representative nucleic acid molecules of the genome which can be used on microarrays to facilitate transcription profile studies. Such studies can help to identify regulatory networks and genes of interest in, for example, production of secondary metabolites, cell-to-cell signaling, cellular differentiation, and motility.

In addition, the *M. xanthus* genome fragments and sequences provided herein permit the fabrication of a wide variety of DNA constructs useful for imparting unique genetic properties into transgenic organisms. These and other advantages attendant with the various aspects of this invention will be apparent from the following description of the invention and its various embodiments.

SUMMARY OF THE INVENTION

The present invention contemplates and provides nucleic acid molecules comprising a substantial part of the genome of the bacterium *Myxococcus xanthus*. One aspect of the invention is a set of 1849 contig and singleton sequences comprising coding sequences, DNA replication elements, as well as promoters and other regulatory elements, such sequences being represented herein as SEQ ID NO: 1 through SEQ ID NO: 1849. Contigs in SEQ ID NO: 1 through SEQ ID NO: 1849 are recognized as those sequences whose designations begin with MYX10C. Singleton sequences are recognized as those having designations that begin with MYX10S. The present invention also encompasses complements of the nucleic acid sequences provided herein. Thus, a subset of the nucleic acid molecules of this invention comprises DNA protein encoding regions, replication elements, promoters and/or other regulatory elements of the *M. xanthus* genome as present in SEQ ID NO: 1 through SEQ ID NO 1849 or complements thereof.

Another aspect of this invention comprises a set of about 7842 genes or partial genes of the *M. xanthus* genome including genes represented by SEQ ID NO: 1850 through SEQ ID NO: 9691 and described in Table 1. As used herein, a substantially complete set of genes for an organism is referred to as a unigene set. Thus, as used herein reference is made to specific genes comprising the unigene set of *M. xanthus* as "MYX12U_xxxx" where MYX12U is an acronym for *Myxococcus xanthus* unigene and xxxx represents a number. Moreover, the term "MYXU" by itself is also used herein to mean any of the nucleic acid molecules comprising genes or partial genes of the unigene set for *M. xanthus*. More particularly the term "MYXU of this invention" as used herein means a nucleic acid molecule representing a gene or partial gene of *M. xanthus* disclosed herein selected from the group consisting of SEQ ID NO: 1850 through SEQ ID NO: 9691. Preferred aspects of this invention contemplate MYXUs as identified by value of the gene prediction method, i.e., BLASTX or GeneMark. Certain preferred MYXUs have a BLASTX Bit Score of at least 100, more preferably 150. Other preferred MYXUs have a GeneMark Probability Score of at least 0.6, more preferably at least 0.75. Still other preferred MYXUs have a BLASTX Bit Score of at least 100 and a GeneMark Probability Score of 0.6; more preferably, respective scores of 150 and 0.75.

The present invention also contemplates and provides substantially purified nucleic acid molecules comprising the MYXUs and other nucleic acid molecules of this invention as well as molecules which are complementary to, and capable of specifically hybridizing to, an MYXU or its complement.

The present invention also contemplates and provides substantially purified nucleic acid molecules which are homologous to the nucleic acid molecules of this invention including, for example, those which are homologous to the MYXUs of this invention, e.g., a plurality of related sets of homologous nucleic acid molecules in other species which are homologous to the MYXUs.

The present invention also contemplates and provides substantially purified protein, or polypeptide fragments thereof, which are encoded by nucleic acid molecules of the present invention. Of particular interest is the group of 7134 *Myxococcus* proteins, peptides or fragments provided herein as SEQ ID NO: 9692 through SEQ ID NO:16825 and designated as MYX12_xxxx_prot, where xxxx is a number corresponding to the MYXU nucleic acid sequence which encodes the peptide.

The present invention also contemplates and provides constructs comprising DNA replication elements, promoters, regulatory elements and/or protein encoding regions that are useful in making transgenic cells or organisms. In particular this invention also provides transformed cells or organisms having a nucleic acid molecule which comprises: (a) a promoter region which functions in the cell to cause the production of an mRNA molecule, which is linked to (b) a structural nucleic acid molecule, which is linked to (c) a 3' non-translated sequence that functions in the cell to cause termination of transcription, where components (a) and/or (b) are selected from *M. xanthus* nucleic acid sequences provided herein and more preferably where component (b) is selected from *M. xanthus* nucleic acid sequences which encode the peptide sequences, provided herein as SEQ ID NO:9692 through SEQ ID NO:16825.

Other aspects of this invention include oligonucleotides (and subsets thereof) for amplification or detection of the nucleic acid molecules of this invention. Such oligonucleotides may be used in analysis of *Myxococcus* gene expression patterns, either as probes or as elements on gene arrays, or to generate and isolate nucleic acid molecules representative of *M. xanthus* genes of this invention and homologs thereof in other myxobacteria species. Thus, the nucleic acids molecules of this invention including the oligonucleotides provided, represent a useful tool in genetic research not only for *M. xanthus*, but also for other bacterial species, particularly for other myxobacteria.

The present invention also contemplates and provides computer readable media having recorded thereon one or more of the nucleotide sequences provided by this invention and methods for using such media, e.g. in searching to identify genes associated with nucleic acid sequences.

The present invention also contemplates and provides collections of nucleic acid molecules, including oligonucleotides, representing the M. xanthus genome including collections on solid substrates, e.g. substrates having attached thereto in array form nucleic acid molecules or oligonucleotides representing genes of the M. xanthus genome. The invention also contemplates and provides methods of using such collections and arrays, e.g. in transcription profiling analysis. The present invention also contemplates and provides methods for using the nucleic acid molecules of this invention, e.g. for identifying genetic material and/or determining gene expression by hybridizing expressed and labeled nucleic acid molecules or fragments thereof to arrayed collections of the nucleic acid molecules of this invention.

The present invention also contemplates and provides oligonucleotides which are identical or complementary to a sequence of similar length in an MYXU. Such oligonucleotides are useful, for example, for hybridizing to and identifying nucleic acid molecules which are homologous and/or complementary to the MYXUs of the present invention.

Other aspects of this invention contemplate methods of using the MYXUs, e.g., for determining gene expression, for identifying mutations in a gene of interest and for constructing mutations in a gene of interest.

DETAILED DESCRIPTION OF THE INVENTION

As used herein, a nucleic acid molecule and/or polypeptide molecule, be it a naturally occurring molecule or otherwise, may be "substantially purified," if the molecule is separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The MYXUs and other nucleic acid molecules and/or polypeptide molecules of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

As used herein the term "polypeptide" means a protein or fragment thereof expressed by a nucleic acid molecule in a cell, or expressed from a nucleic acid molecule in vitro, i.e. by in vitro translation.

The MYXUs and other nucleic acid molecules of the present invention may also be recombinant. As used herein, the term recombinant means any molecule (e.g. DNA, peptide etc.), that is, or results, however indirect, from human manipulation of a nucleic acid molecule.

Of particular interest are MYXUs of the present invention which encode proteins involved in the production of polyketides. Polyketides are a class of small bioactive molecules that are linked by their biosynthetic pathways (sequence of reactions). The pathways and their products are particularly abundant in soil microorganisms, including Myxococcus xanthus. A large number of major pharmaceutical and agricultural products have been derived from these complex natural products including insecticides, fungicides, antibacterial agents, anti-inflammatory agents, cancer-fighting agents, and cholesterol-lowering agents. Examples of polyketides include Rifamycins (Rifampin), Adriamycin (Doxorubicin), Erythromycin, Mevacor (Lovastatin), Ascomycin (Immunomycin), and Spinosad.

The production of polyketides is catalyzed by the activity of a family of large proteins designated as polyketide synthases or synthetases, which are also sometimes referred to as peptide synthetases, nonribosomal peptide synthetases or ketoacyl synthases. Additional enzymes, such as reductases, are also involved in the synthesis pathways of polyketides. Analysis of the sequences provided herein reveals the existence of an extraordinarily large number of Myxococcus genes that encode polyketide synthases. In addition, there are a substantial number of open reading frames with homology to the NosAB proteins from Nostoc species. These proteins, in combination with NosC and NosD proteins, form a pathway for nostopeptolide, a polyketide synthase (or synthetase) related to the tyrocidine synthetase 3 of Brevibacillus brevis and the syringomycin synthetase of Pseudomonas syringae. The Nostoc NosA proteins also are homologous to the Nostoc NosC and NosD proteins. The NosB protein is homologous to the McyG protein of Microcystis aeruginosa and the MtaD Stigmatella aurantiaca. The Mta genes are members of the myxothiazol biosynthetic gene cluster involved in the production of a number of well known polyketides in Stigmatella species.

Additional Myxococcus genes are homologous to genes in the epothilone biosynthetic gene cluster from Sorangium cellulosum. Epothilones are polyketide natural products that have been shown to have use as anti-cancer agents. They inhibit cancer cells by the same mechanism as the taxanes, and have the advantage that they are effective against many taxane resistant tumors. The genes encoding the PKS in this cluster are epoA, epoC, epoD, epoE, and epoF. The EpoB protein is a non-ribosomal peptide synthetase (NRPS) that catalyzes formation of the thiazole found in the epothilones. EpoK is a P450 enzyme responsible for the epoxidation of epothilones C and D to epothilones A and B, respectively.

Analysis of Myxococcus xanthus using codori preference tables suggests that this organism is remarkably distant from all other known sequenced organisms. In addition, genome signature analysis suggests that little horizontal transfer has occurred. It is thus likely that many of the polyketides encoded by Myxococcus genes will have novel characteristics in comparison to known polyketides from other organisms. In addition, it is likely that different polyketides will be produced in Myxococcus under different growth conditions.

The polyketide synthase encoding genes provided herein can be placed into the genome of a plant to produce a polyketide substance that can protect a plant against damage from insects, fungi, or bacteria. In addition, these genes can be placed in plants or other organisms to generate polyketides for other uses, including for discovery and production of pharmaceuticals.

Genes from Myxococcus xanthus that are involved in the nitrogen pathway are also provided in the present invention. Oxidized nitrogen in the biosphere must be reduced to ammonia for use by all organisms. The most common oxidized form of nitrogen is nitrate ($NO3^-$). Nitrate must be reduced through nitrite (NO2⁻) to ammonia (NH3). Genes for nitrate reduction are found in plants and microorganisms. Two reactions are required for this reductive pathway. The first, nitrate reductase, reduces nitrate to nitrite and the second, nitrite reductase, converts nitrite to ammonia. The conversion of nitrite to ammonia is the often the rate limiting step to nitrogen assimilation so addition of genes that can improve this reduction should improve nitrogen assimilation and thus yield. Transcriptional expression of these genes in plants is usually suppressed by the presence of reduced nitrogen (ammonia or glutamine). The expression of bacterial genes in plants is a method to overcome the transcriptional expression barriers. *Myxococcus* genes encoding nitrate/nitrite transporters are also of interest. Nitrogen fertilizers are often in the form of ammonium nitrate. Addition of nitrate or nitrite uptake systems and their reductive pathways can be used to lower the use of fertilizers in the soil resulting in lower crop production costs for farmers. Thus, *Myxococcus* genes encoding nitrate and nitrite reductases, nitrate/nitrite transporters, such as ABC transporters, and regulatory proteins in the nitrate pathway, such as sigma-54 dependent transcriptional activators, are of use for production of plants having improved nitrate utilization and increased yield.

*Myxococcus xanthus* genes encoding serine threonine protein kinases are also provided in the present invention. Protein kinases play roles in the regulation of protein and enzyme activity in the transduction of environmental, developmental, and metabolic signals in animals and simple eukaryotes. It has been reported that protein kinases also act as signal transducers in plants, and activities of plant protein kinases have been reported to be responsive to various environmental stimuli and developmental changes. A majority of the reported plant protein kinases are serine threonine protein kinases. Serine threonine protein kinases are not generally present in microbes, but analysis of the genome of *Myxococcus xanthus* reveals the presence of a substantial number of genes encoding serine threonine protein kinases. Such genes are of interest for use in production of transgenic plants and microorganisms to produce plants and microorganisms having altered growth and development patterns, and particularly for providing organisms having improved responses to environmental stresses. Such modifications are of particular interest for increasing the yield of crop plants.

The present invention also provides *Myxococcus xanthus* genes that encode sigma factors. Sigma factors are prokaryotic transcription factors that bind to DNA and help initiate transcription by recruiting RNA polymerase and inducing helix unwinding. These gene products might be used to alter the regulatory pathways of microorganisms or to better express prokaryotic genes that are used in transgenic organisms.

Also of interest in the present invention are *Myxococcus* genes encoding antiobiotic resistance proteins. Such genes may be used, for example, as markers for selecting transgenic organisms, such as plants, animals, fungi or bacteria, so that genes linked to these markers can be introduced into the target organism. Alternatively, such markers can be used as a counter-selection, i.e. to select against the donor of a transgenic cross. Additional genes that find use as markers for selection of transgenic organisms are genes encoding proteins which confer resistance to UV light, such as UVR genes.

Additional classes of proteins encoded by genes of the present invention are readily apparent by examination of the sequences and the associated annotations provided in Table 1 here. Another example of genes of particular interest in the present invention are genes encoding DNA methylases and restriction enzymes. Such proteins can be used in DNA technology to alter DNA for manipulations such as DNA isolation for cloning and the polymerase chain reaction.

It is understood that the nucleic acid molecules of the present invention may be labeled with reagents that facilitate detection of the nucleic acid molecules, e.g. fluorescent labels as disclosed in U.S. Pat. No. 4,653,417, chemical labels as disclosed in U.S. Pat. Nos. 4,582,789 and 4,563,417 and modified bases as disclosed in U.S. Pat. No. 4,605,735, all of which are incorporated herein by reference in their entirety.

The term "oligonucleotide" as used herein refers to short nucleic acid molecules useful, e.g. for hybridizing probes, nucleotide array elements, sequencing primers, or primers for DNA extension reactions, such as polymerase chain reaction. The size of the oligonucleotide molecules of the present invention will depend upon several factors, particularly on the ultimate function or use intended for a particular oligonucleotide. Oligonucleotides, i.e. deoxyribonucleotides or ribonucleotides, can comprise ligated natural nucleic acid molecules or synthesized nucleic acid molecules and will generally comprise between 5 to 150 nucleotides or between about 15 and about 100 nucleotides, or preferably up to 100 nucleotides, and even more preferably between 15 to 30 nucleotides or most preferably between 18–25 nucleotides. The sequence of the oligonucleotides will ideally be identical or complementary to the sequence of a fragment of similar length in a *Myxococcus* nucleic acid molecule provided herein.

This invention provides oligonucleotides specific for nucleic acid molecules of the present invention. Such oligonucleotides find particular use as nucleic acid elements for use on solid arrays (e.g. synthesized or spotted), as hybridization probes, and as primers for amplification of protein encoding regions of this invention. Oligonucleotides for use in polymerase chain reaction (PCR) primers are preferably designed with the goal of amplifying nucleic acids from either the 3' or the 5' end of an *M. xanthus* gene or gene fragment, e.g. about 500 to 800 bp of nucleic acids.

The term "primer" as used herein refers to a nucleic acid molecule, preferably an oligonucleotide whether derived from a naturally occurring molecule, such as one isolated from a restriction digest, or one produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer. For example, depending on the complexity of the target sequence, the oligonucleotide primer typically contains at least 15, more preferably 18 nucleotides, which are identical or complementary to the template and optionally a tail of variable length which need not match the template. The length of the tail should not be so long that it interferes with the recognition of the template. Short primer molecules generally require cooler temperatures to form sufficiently stable hybrid complexes with the template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer. Computer generated search programs such as Primer3 (Steve Rozen, Helen J. Skaletsky (1996,1997); code available at genome.wi.mit.edu/genome_software/other/primer3, STSPipeline genome.wi.mit.edu/cgi-bin/STS Pipeline), or GeneUp (Pesole et al., *BioTechniques* 25:112–123 (1998)), for example, can be used to identify potential PCR primers. Exemplary primers include primers that are 18 to 50 bases long, where at least between 18 to 25 bases are identical or complementary to a segment of corresponding length in the template sequence. Preferred template sequences for such primers are selected from MYXO sequences provided herein as SEQ ID NO: 1850 through SEQ ID NO: 9691 or complements thereof, particularly those sequences which encode peptides whose sequences are provided herein as SEQ ID NO: 9692 through SEQ ID NO: 16825.

This invention also contemplates and provides primer pairs for amplification of nucleic acid molecules representing *Myxococcus* genes. As used herein "primer pair" means a set of two oligonucleotide primers based on two separated sequence segments of a target nucleic acid sequence. One primer of the pair is a "forward primer" or "5' primer" having a sequence which is identical to the more 5' of the separated sequence segments. The other primer of the pair is a "reverse primer" or "3' primer" having a sequence which is complementary to the more 3' of the separated sequence segments. A primer pair allows for amplification of the nucleic acid sequence between and including the separated sequence segments. Optionally, each primer pair can comprise additional sequences, e.g. universal primer sequences or restriction endonuclease sites, at the 5' end of each primer, e.g. to facilitate cloning, DNA sequencing, or reamplification of the target nucleic acid sequence.

Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure along a sufficient portion of the molecule to allow for stable binding under laboratory hybridizing conditions. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning*, A Laboratory Manual, 2nd Ed., Cold Spring Harbor Press, Cold Spring Harbor, N.Y. (1989), and by Haymes et al., *Nucleic Acid Hybridization*, A Practical Approach, IRL Press, Washington, D.C. (1985), the entirety of both of which are herein incorporated by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, incubation in 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Preferred embodiments of the nucleic acid of this invention will specifically hybridize to one or more of the nucleic acid molecules of this invention or complements thereof under low stringency conditions, for example at about 2.0×SSC and about 50° C. In a particularly preferred embodiment, a nucleic acid of the present invention will include those nucleic acid molecules that specifically hybridize to one or more of the nucleic acid molecules of this invention or complements thereof under moderate stringency conditions. In an especially preferred embodiment, a nucleic acid of the present invention will include those nucleic acid molecules that specifically hybridize to one or more of the nucleic acid molecules of this invention or complements thereof under high stringency conditions.

In another aspect of the present invention, one or more of the nucleic acid molecules of the present invention share between 100% and 90% sequence identity with one or more of the *Myxococcus* nucleic acid molecules of this invention or complements thereof. In a further aspect of the present invention, one or more of the nucleic acid molecules of the present invention share between 100% and 95% sequence identity with one or more of the *Myxococcus* nucleic acid molecules of this invention or complements thereof. In a more preferred aspect of the present invention, one or more of the nucleic acid molecules of the present invention share between 100% and 98% sequence identity with one or more of the *Myxococcus* nucleic acid molecules of this invention or complements thereof. In an even more preferred aspect of the present invention, one or more of the nucleic acid molecules of the present invention share between 100% and 99% sequence identity with one or more of the *Myxococcus* nucleic acid molecules of this invention or complements thereof.

The present invention also encompasses the use of nucleic acids of the present invention in recombinant constructs. Using methods known to those of ordinary skill in the art, a protein encoding sequence and/or a promoter sequence of the invention can be inserted into constructs which can be introduced into a host cell of choice for expression of the encoded protein, if an encoding sequence is used, or for use of an *M. xanthus* promoter to direct expression of a heterologous protein. Potential host cells include both prokaryotic and eukaryotic cells. A host cell may be unicellular or found in a multicellular differentiated or undifferentiated organism depending upon the intended use. It is understood that useful exogenous genetic material may be introduced into any cell or organism such as a bacterial cell, fungal cell, fungus, plant cell, plant, mammalian cell, mammal, fish cell, fish, bird cell, bird or bacterial cell.

Depending upon the host, the regulatory regions for expression of *Myxococcus* sequences, particularly MYXU sequences, will vary, including regions from viral, plasmid or chromosomal genes, or the like. For expression in prokaryotic or eukaryotic microorganisms, particularly unicellular hosts, a wide variety of constitutive or regulatable promoters may be employed. Among transcriptional initiation regions which have been described are those obtained from bacterial and yeast hosts, such as *E. coli, B. subtilis*, and *Sacchromyces cerevisiae*, including genes such as beta-galactosidase, T7 polymerase and tryptophan E.

Furthermore, for use in transformation of *M. xanthus*, constructs may include those in which a *Myxococcus* protein encoding sequence or portion thereof of the present invention is positioned with respect to a promoter sequence such that production of antisense mRNA complementary to native mRNA molecules is provided. In this manner, expression of the native gene may be decreased. Such methods may find use for modification of particular functions of the targeted host, and/or for discovering the function of a protein naturally expressed in *M. xanthus*.

The present invention also encompasses the use of nucleic acids of the present invention in constructs which provide for mutation of genes within *M. xanthus* by homologous recombination. Such constructs, for example, may contain two regions of a protein encoding sequence harboring a heterologous portion of DNA (such as an antibiotic resistance marker) between the two encoding segments. Such constructs may also contain, for example, other deletions, insertions, or base changes, or combinations thereof, relative to the *M. xanthus*-derived DNA sequence. Introduction of these constructs into *M. xanthus* can be used to generate mutations in the DNA of *M. xanthus*. Such directed mutations are useful, for example, for functional analysis of the mutated genes.

Homologs of MYXUs

Genomic sequences can be screened for the presence of nucleic acid and/or protein homologs utilizing one or a number of different search algorithms that have been developed, one example of which are the suite of programs referred to as BLAST programs. In addition, unidentified reading frames may be discovered using gene prediction software such as GenScan (available for downloading from the Stanford University web site) or GeneMark. In this manner, novel homologs of the nucleic acid and/or peptide sequences of the present invention are provided, including homologs from plant, animal, fungal or bacterial organism, including other *Myxococcus* species and other myxobacteria. Of particular interest are nucleic acid molecules which encode polypeptides which are homologous to polypeptides encoded by *Myxococcus* protein encoding regions of this invention where the percent identity between the polypeptides is between about 25% and about 40%, more preferably of between about 40% and about 70%, even more preferably of between about 70% and about 90%, and even more preferably between about 90% and 99% and most preferably 100%.

The degeneracy of the genetic code allows different nucleic acid sequences to code for the same protein or peptide, e.g. see U.S. Pat. No. 4,757,006, the entirety of which is herein incorporated by reference. As used herein a nucleic acid molecule is degenerate of another nucleic acid molecule when the nucleic acid molecules encode for the same amino acid sequences but comprise different nucleotide sequences. An aspect of the present invention is that the nucleic acid molecules of the present invention include nucleic acid molecules that are degenerate from the *Myxococcus* protein encoding regions of this invention.

A further aspect of the present invention comprises one or more nucleic acid molecules which differ in nucleic acid sequence from those of a *Myxococcus* protein encoding region of this invention in that they encode the same protein but differ in nucleic acid sequence and protein sequence as the result of one or more conservative amino acid substitutions, deletions or insertions. Codons capable of coding for conservative substitutions are known in the art. For instance, serine is a conservative substitute of alanine and threonine is a conservative substitute for serine.

Regulatory Elements

One class of agents of the present invention includes nucleic acid molecules having promoter regions or partial promoter regions or other regulatory elements, particularly those found in SEQ ID NO: 1 through SEQ ID NO: 1849 and located upstream of translational initiation codon sequence at the start site of a protein coding region. Translational initiation codons in bacteria are most commonly AUG, occasionally GUG, or rarely, UUG or AUU. As used herein, a promoter region is a region of a nucleic acid molecule that is capable, when located in cis to a nucleic acid sequence that encodes for a protein or peptide to function in a way that directs transcription of one or more mRNA molecules that encodes for the protein or peptide. Promoters may be located directly 5' to the protein encoding sequence, for example where a promoter regulates transcription of a single gene. Alternatively, such as when a promoter regulates transcription of a group of genes in an operon, the promoter may be located some distance upstream from a particular encoding region. Promoters of the present invention will generally be recognized by their presence 5' to, or upstream, of the start site for a protein coding region and/or by the presence of the −10 and −35 consensus core promoter elements found in bacterial promoters. In addition, promoters of the present invention may contain additional non-core sequences which can affect promoter strength. Such additional regulatory sequences may be located upstream of, downstream of, or between core promoter elements. Examples of additional regulatory elements include UP elements (−40 upstream region) and DSR elements (region immediately downstream of the transcription start site).

In a preferred embodiment, the promoter of the present invention is present in a recombinant construct and located upstream of a nucleic acid sequence for expression in *M. xanthus* cells, including nucleic acid sequences that encode an *M. xanthus* protein homolog or fragment thereof. For the most part, the promoters of the present invention will be located in contig sequences which generally represent longer nucleic acids than do singleton sequences of the present invention. Contigs in SEQ ID NO: 1 through SEQ ID NO: 1849 are recognized as those sequences whose designations begin with MYX10C, as opposed to singletons whose designations begin with MYX10S.

DNA Replication Elements

The present invention further encompasses *Myxococcus xanthus* DNA replication elements, such as the origin of replication from which replication proceeds, and the terminus, or ter site on the circular chromosome. (Marians, *Annu. Rev. Biochem* 61:673–719 (1992)). The origin or replication may be recognized by the presence of conserved DNA structures Eckdahl et al., *Nucleic Acids Res.* 18:1609–12 (1990); Moriya et al., *Saibo Kogaku* 15:13–22 (1996); *Network Sci.* [Electronic Publication] (1995), 1(4, Avail. URL: http://www.awod.com/netsci/Issues/Oct95/feature4.html). As increased gene dosage has been suggested to occur near origin of replication and ter sites under certain doubling time conditions, identification of such sites is useful for use for insertion of recombinant DNA constructs for expression in *Myxococcus* cells.

Polypeptides

Other aspects of this invention comprise one or more of the polypeptides, including proteins or peptide molecules, encoded by a *Myxococcus* coding region of this invention or fragments thereof or homologs thereof. Coding regions and the encoding protein or peptide molecules of the present invention can be identified using known protein or peptide molecules as a target sequence or target motif, for example using BLAST programs as described herein. In a preferred embodiment the protein or fragment molecules of the present invention are derived from *M. xanthus*, particularly those protein molecules having amino acid sequences provided herein as SEQ ID NO: 9692 through SEQ ID NO: 16825.

As used herein, the terms "protein molecule" or "peptide molecule" include any molecule that comprises five or more amino acids. It is well known in the art that proteins or peptides may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acid" and "amino acids" refer to all naturally occurring L-amino acids. This definition is meant to include norleucine, ornithine, homocysteine, and homoserine.

One or more of the protein or peptide molecules may be produced via chemical synthesis, or more preferably, by expression in a suitable bacterial or eukaryotic host. Suitable methods for expression are described by Sambrook et al., *Molecular Cloning, A Laboratory Manual*, 2nd Edition, Cold Spring Harbor Press, Cold Spring Harbor, N.Y. (1989), or similar texts.

A "protein fragment" comprises a subset of the amino acid sequence of that protein. A protein fragment which comprises one or more additional peptide regions not derived from a base protein is a "fusion" protein. Such molecules may be derivatized to contain carbohydrate or other groups (such as keyhole limpet hemocyanin, etc.). Fusion protein or peptide molecules of the present invention are preferably produced via recombinant means.

Another class of agents comprises protein or peptide molecules encoded by the coding regions of this invention or, fragments or fusions thereof in which conservative, non-essential, or irrelevant, amino acid residues are present, substituted or deleted either by intentional manipulation of the peptide or underlying encoding sequence, or as a naturally present homolog in a related organism, for example in a *M. xanthus* strain that is other than the *M. xanthus* disclosed herein. Such a homolog can be obtained by any of a variety of methods. For example, as indicated above, one or more of the disclosed sequences for primers of this invention can be used to define a pair of primers that may be used to isolate the homolog-encoding nucleic acid molecules from any desired species. Such molecules can be expressed to yield homologs by recombinant means.

Antibodies

One aspect of the present invention concerns antibodies, single-chain antigen binding molecules, or other proteins that specifically bind to one or more of the protein or peptide molecules of the present invention and their homologs, fusions or fragments. Such antibodies may be used to quantitatively or qualitatively detect the protein or peptide molecules of the present invention. As used herein, an antibody or peptide is said to "specifically bind" to a protein or peptide molecule of the present invention if such binding is not competitively inhibited by the presence of non-related molecules. In a preferred embodiment the antibodies of the present invention bind to proteins of the present invention, in a more preferred embodiment of the antibodies of the present invention bind to proteins derived from *M. xanthus*.

Nucleic acid molecules that encode all or part of the proteins of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be "fusion" molecules (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal. It is understood that practitioners are familiar with the standard resource materials which describe specific conditions and procedures for the construction, manipulation and isolation of antibodies (see, for example, Harlow and Lane, *Antibodies: A Laboratory Manual*, Cold Spring Harbor Press, Cold Spring Harbor, N.Y. (1988), the entirety of which is herein incorporated by reference).

It is understood that any of the antibodies of the present invention can be substantially purified and/or be biologically active and/or recombinant.

Recombinant Vectors and Transformants

A further aspect of the present invention relates to recombinant vectors comprising nucleic acid molecules of the present invention. In a preferred embodiment a recombinant vector includes at least one nucleic acid molecule of the present invention which can preferably be (a) a protein encoding region of this invention or fragment or homolog thereof, (b) a regulatory element, promoter or partial promoter, or (c) a DNA replication element of the present invention. In a further preferred embodiment of the present invention, a recombinant vector includes a regulatory element, promoter or partial promoter of the present invention and a protein encoding region of the present invention, such nucleic acid molecules of the present invention having a sequence within a contig or singleton within the group identified by SEQ ID NO: 1 through SEQ ID NO: 1849 or complements thereof or fragments of either. In a further more preferred embodiment of the present invention, the recombinant vector includes a regulatory element, promoter or partial promoter of the present invention and a nucleic acid molecule encoding an *M. xanthus* protein or fragment thereof, for example the corresponding promoter for a MYXU which promoter may be identified and obtained from the source contig or singleton for the MYXU.

Preferably, such recombinant vectors of the present invention are introduced into a *Myxococcus* species cell, more preferably an *M. xanthus* cell, particularly an *M. xanthus* DK1622 cell. It is also understood that such recombinant vectors may also be introduced into any other cell or organism, including a plant cell, plant, fungal cell, fungus, mammalian cell, mammal, fish cell, fish, bird cell, bird or other (non-*Myxococcus*) bacterial cell, so long as appropriate components, such as functional promoters, replication elements, and selectable markers are selected for the particular host to be transformed.

The recombinant vector of this invention may be any vector which can be conveniently subjected to recombinant DNA procedures. The choice of a vector will typically depend on the compatibility of the vector with the host cell into which the vector is to be introduced. The vector may be a linear or a closed circular plasmid. The vector system may be a single vector or plasmid or two or more vectors or plasmids which together contain the total DNA to be introduced into the genome of the host. Methods which can be used to introduce recombinant vectors into *Myxococcus* species include triparental mating (Ditta et al., *Plasmid* 13:149–153 (1985); Ditta et al., *Proc. Natl. Acad. Sci. USA* 77:7347–7351 (1980)), electroporation (White et al., *Meth in Mol. Biol.* 47:135–141 (1995)) and P1 Transduction (Avery et al., *Mol. Gen. Genet.* 191:99–109 (1983)).

The vectors of the present invention preferably contain one or more selectable markers which permit easy selection of transformed cells. A selectable marker is a gene whose product provides, for example, biocide or viral resistance, resistance to heavy metals, prototrophy to auxotrophs, and the like. Various selectable markers may be used depending upon the host species to be transformed, and different conditions for selection may be used for different hosts.

A nucleic acid sequence of the present invention may be operably linked to a suitable promoter sequence. A nucleic acid molecule of the present invention that encodes a protein or fragment thereof may also be operably linked to a suitable leader sequence. A leader sequence may be a nontranslated region of an mRNA which is important for translation by a host cell. A leader sequence is operably linked to the 5' terminus of the nucleic acid sequence encoding the protein or fragment thereof. The leader sequence may be native to the nucleic acid sequence encoding the protein or fragment thereof or may be obtained from foreign sources. A polyadenylation sequence may also be operably linked to the 3' terminus of the nucleic acid sequence of the present invention, particularly for use in eukaryotic host cells.

To avoid the necessity of disrupting the cell to obtain the protein or fragment thereof, and to minimize the amount of possible degradation of the expressed protein or fragment thereof within the cell, it may be preferred that expression of the protein or fragment thereof gives rise to a product secreted outside the cell, especially in the case of expression in bacterial host cells of bacterium or bacteria. To this end, the protein or fragment thereof of the present invention may be linked to a signal peptide linked to the amino terminus of the protein or fragment thereof. A signal peptide is an amino acid sequence which permits the secretion of the protein or fragment thereof from the host into the culture medium.

A protein or fragment thereof encoding a nucleic acid molecule of the present invention may also be linked to a propeptide coding region. A propeptide is an amino acid sequence found at the amino terminus of apoprotein or proenzyme. Cleavage of the propeptide from the proprotein yields a mature biochemically active protein. The resulting polypeptide is known as a propolypeptide or proenzyme (or a zymogen in some cases). Propolypeptides are generally inactive and can be converted to mature active polypeptides by catalytic or autocatalytic cleavage of the propeptide from the propolypeptide or proenzyme. The propeptide coding region may be native to the protein or fragment thereof or may be obtained from foreign sources.

A protein or fragment thereof encoding a nucleic acid molecule of the present invention may also be linked to a transit peptide coding region. A transit peptide is an amino acid sequence found at the amino terminus of an active protein which provides for transport of the protein into a plastid organelle, such as a plant chloroplast. The transit peptide coding region may be native to the type of cell to be transformed, or may be obtained from foreign sources.

An expressed protein or fragment thereof of the present invention may be detected using methods known in the art that are specific for the particular protein or fragment. These detection methods may include the use of specific antibodies, formation of an enzyme product, or disappearance of an enzyme substrate. For example, if the protein or fragment thereof has enzymatic activity, an enzyme assay may be used. Alternatively, if polyclonal or monoclonal antibodies specific to the protein or fragment thereof are available, immunoassays may be employed using the antibodies to the protein or fragment thereof. The techniques of enzyme assay and immunoassay are well known to those skilled in the art.

The resulting protein or fragment thereof may be recovered by methods known in the arts For example, the protein or fragment thereof may be recovered from the nutrient medium by conventional procedures including, but not limited to, centrifugation, filtration, extraction, spray-drying, evaporation, or precipitation. The recovered protein or fragment thereof may then be further purified by a variety of chromatographic procedures, e.g., ion exchange chromatography, gel filtration chromatography, affinity chromatography, or the like.

Plant Constructs and Plant Transformants

Of particular interest is the use of nucleic acid molecules of this invention for plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. Such genetic material may be transferred into either monocotyledons and dicotyledons including but not limited to the plants, alfalfa, *Arabidopsis thaliana*, barley, broccoli, cabbage, citrus, cotton, garlic, oat, oilseed rape, onion, canola, flax, maize, an ornamental plant, pea, peanut, pepper, potato, rice, rye, sorghum, soybean, strawberry, sugarcane, sugarbeet, tomato, wheat, poplar, pine, fir, eucalyptus, apple, lettuce, lentils, grape, banana, tea, turf grasses, sunflower, oil palm, etc.

A variety of methods can be used to generate stable transgenic plants. These include particle gun bombardment (Fromm et al, *Bio/Technology* 8:833–839 (1990)), electroporation of protoplasts (Rhodes et al., *Science* 240:204–207 (1989); Shimamoto et al., *Nature* 338:274–276 (1989)), treatment of protoplasts with polyethylene glycol (Datta et al., *Bio/Technology,* 8:736–740 (1990)), microinjection (Neuhaus et al, *Theoretical and Applied Genetics,* 75:30–36 (1987)), immersion of seeds in a DNA solution (Ledoux et al., *Nature,* 249:17–21 (1974)), and transformation with T-DNA of *Agrobacterium* (Valvekens et al., *PNAS,* 85:5536–5540 (1988); Komari, *Plant Science,* 60:223–229 (1989)). In most, perhaps all plant species, *Agrobacterium*- mediated transformation is the most efficient and easiest of these methods to use. T-DNA transfer generally produces the greatest number of transformed plants with the fewest multi-copy insertions, rearrangements, and other undesirable events.

Many different methods for generating transgenic plants using *Agrobacterium* have been described. In general, these methods rely on a "disarmed" *Agrobacterium* strain that is incapable of inducing tumors, and a binary plasmid transfer system. The disarmed strain has the oncogenic genes of the T-DNA deleted. A Binary plasmid transfer system consists of one plasmid with the 23-base pair T-DNA left and right border sequences, between which a gene for a selectable marker (e.g. an herbicide resistance gene) and other desired genetic elements are cloned. Another plasmid encodes the *Agrobacterium* genes necessary for effecting the transfer of the DNA between the border sequences in the first plasmid. Plant tissue is exposed to *Agrobacterium* carrying the two plasmids, the DNA between the left and right border repeats is transferred into the plant cells, transformed cells are identified using the selectable marker, and whole plants are regenerated from the transformed tissue. Plant tissue types that have been reported to be transformed using variations of this method include: cultured protoplasts (Komari, *Plant Science*, 60:223–229 (1989)), leaf disks (Lloyd et al., *Science* 234:464–466 (1986)), shoot apices (Gould et al., *Plant Physiology*, 95:426–434 (1991)), root segments (Valvekens et al., *PNAS*, 85:5536–5540 (1988)), tuber disks (Jin et al., *Journal of Bacteriology*, 169: 4417–4425 (1987)), and embryos (Gordon-Kamm et al., *Plant Cell*, 2:603–618 (1990)).

In the case of *Arabidopsis thaliana* it is possible to perform in planta germline transformation (Katavic et al., *Molecular and General Genetics*, 245:363–370 (1994); Clough et al., *Plant Journal*, 16:735–743 (1998)). In the simplest of these methods, flowering *Arabidopsis* plants are dipped into a culture of *Agrobacterium* such as that described in the previous paragraph. Among the seeds produced from these plants, 1% or more have integration of T-DNA into the genome.

Monocot plants have generally been more difficult to transform with *Agrobacterium* than dicot plants. However, "supervirulent" strains of *Agrobacterium* with increased expression of the virB and virG genes have been reported to transform monocot plants with increased efficiency (Komari et al., *Journal of Bacteriology*, 166:88–94 (1986); Jin et al., *Journal of Bacteriology*, 169:417–425 (1987)).

Most T-DNA insertion events are due to illegitimate recombination events and are targeted to random sites in the genome. However, given sufficient homology between the transferred DNA and genomic sequence, it has been reported that integration of T-DNA by homologous recombination may be obtained at a very low frequency. Even with long stretches of DNA homology, the frequency of integration by homologous recombination relative to integration by illegitimate recombination is roughly 1:1000 (Miao et al., *Plant Journal*, 7:359–365 (1995); Kempin et al, 389:802–803 (1997)).

Exogenous genetic material may be transferred into a plant cell by the use of a DNA vector or construct designed for such a purpose. Vectors have been engineered for transformation of large DNA inserts into plant genomes. Binary bacterial artificial chromosomes have been designed to replicate in both *E. coli* and *Agrobacterium* and have all of the features required for transferring large inserts of DNA into plant chromosomes. BAC vectors, e.g. a pBACwich, have been developed to achieve site-directed integration of DNA into a genome.

A construct or vector may also include a plant promoter to express the gene or gene fragment of choice. A number of promoters that are active in plant cells have been described in the literature. These include the nopaline synthase (NOS) promoter, the octopine synthase (OCS) promoter, a caulimovirus promoter such as the CaMV 19S promoter and the CaMV 35S promoter, the figwort mosaic virus 35S promoter, the light-inducible promoter from the small subunit of ribulose-1,5-bis-phosphate carboxylase (ssRUBISCO), the Adh promoter, the sucrose synthase promoter, the R gene complex promoter, and the chlorophyll a/b binding protein gene promoter. For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea, the chloroplast fructose-1,6-biphosphatase (FBPase) promoter from wheat, the nuclear photosynthetic ST-LS1 promoter from potato, the phenylalanine ammonia-lyase (PAL) promoter and the chalcone synthase (CHS) promoter from *Arabidopsis thaliana*. Also reported to be active in photosynthetically active tissues are the ribulose-1,5-bisphosphate carboxylase (RbcS) promoter from eastern larch (Larix laricina), the promoter for the cab gene, cab6, from pine, the promoter for the Cab-1 gene from wheat, the promoter for the CAB-1 gene from spinach, the promoter for the cab1R gene from rice, the pyruvate, orthophosphate dikinase (PPDK) promoter from *Zea mays*, the promoter for the tobacco Lhcb1*2 gene, the *Arabidopsis thaliana* SUC2 sucrose-$H^+$ symporter promoter, and the promoter for the thylacoid membrane proteins from spinach (psaD, psaF, psaE, PC, FNR, atpC, atpD, cab, rbcS). Other promoters for the chlorophyl a/b-binding proteins may also be utilized in the present invention, such as the promoters for LhcB gene and PsbP gene from white mustard (*Sinapis alba*). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435 and 4,633,436, all of which are herein incorporated in their entirety.

Constructs or vectors may also include, with the coding region of interest, a nucleic acid sequence that acts, in whole or in part, to terminate transcription of that region. For example, such sequences have been isolated including the Tr7 3' sequence and the nos 3' sequence or the like. It is understood that one or more sequences of the present invention that act to terminate transcription may be used.

A vector or construct may also include other regulatory elements or selectable markers. Selectable markers may also be used to select for plants or plant cells that contain the exogenous genetic material. Examples of such include, but are not limited to, a neo gene which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil, a mutant acetolactate synthase gene (ALS) which confers imidazolinone or sulphonylurea resistance; and a methotrexate resistant DHFR gene.

A vector or construct may also include a screenable marker to monitor expression. Exemplary screenable markers include a β-glucuronidase or uidA gene (GUS), an R-locus gene, which encodes a product that regulates the production of anthocyanin pigments (red color) in plant tissues; a β-lactamase gene, a gene which encodes an enzyme for which various chromogenic substrates are known (e.g., PADAC, a chromogenic cephalosporin); a luciferase gene, a xylE gene which encodes a catechol dioxygenase that can convert chromogenic catechols; an α-amylase gene, a tyrosinase gene which encodes an enzyme capable of oxidizing tyrosine to DOPA and dopaquinone which in turn condenses to melanin; an α-galactosidase, which will turn a chromogenic α-galactose substrate. Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

Thus, any of the nucleic acid molecules of the present invention may be introduced into a plant cell in a permanent or transient manner in combination with other genetic elements such as vectors, promoters enhancers etc. Further any of the nucleic acid molecules encoding an *E. nidulans* protein or fragment thereof or homologs of the present invention may be introduced into a plant cell in a manner that allows for over expression of the protein or fragment thereof encoded by the nucleic acid molecule.

Uses of the Agents of the Present Invention

Nucleic acid molecules and fragments thereof of the present invention may be employed to obtain nucleic acid molecule homologs from other hosts, particularly from other related bacterial species, such as other myxobacteria species. Such related nucleic acid molecules include those that encode, in whole or in part, protein homologs of MYXU encoded proteins, sequences of genetic elements such as promoters and transcriptional regulatory elements, and sequences of DNA replication elements. Such molecules can be readily obtained by using the above-described nucleic acid molecules to screen cDNA or genomic libraries, or by applying PCR. Methods for forming such libraries are well known in the art. Such homolog molecules may differ in their nucleotide sequences from those found in one or more of the *M. xanthus* genes of this invention or complements thereof because complete complementarity is not needed for stable hybridization. The nucleic acid molecules of the present invention therefore also include molecules that, although capable of specifically hybridizing with the nucleic acid molecules may lack "complete complementarity."

The disclosed nucleic acid molecules may be used to define one or more primer pairs that can be used with the polymerase chain reaction to amplify and obtain any desired nucleic acid molecule or fragment thereof. Such molecules will find particular use in generation of nucleic acid arrays, including microarrays, containing portions of or the entire encoding region for the identified *M. xanthus* genes.

The nucleic acid molecules of the present invention may be used in construction of physical and/or genetic maps of *M. xanthus*. Physical mapping, in conjunction with linkage analysis, can enable the isolation of genes and the elucidation of pathways. Nucleic acid molecules of the present invention can also be used in comparative mapping. Comparative mapping within families provides a method to assess the degree of sequence conservation, gene order, ploidy of species, ancestral relationships and the rates at which individual genomes are evolving. By comparing the results obtained by genetic mapping in model organisms, with those from other species, similarities of genomic structure among species can be established.

In a further aspect of the present invention, one or more of the agents of the present invention may be used to detect the presence, absence or level of a organism, such as a *Myxococus* bacterium, particularly a *M. xanthus* bacterium, and more preferably, a *M. xanthus* DK1622 bacterium in a sample. This aspect is of particular use in the development of sensitive and specific methods to assay for low levels of myxobacteria.

In yet another aspect of the present invention, one or more of the nucleic acid molecules of the present invention are used to determine the level (i.e., the concentration of DNA or RNA in a sample, etc.) or pattern (i.e., the timing or kinetics of expression, rate of decomposition, stability profile, etc.) of expression of the encoding sequence for a protein encoded in part or whole by one or more of the nucleic acid molecule of the present invention (collectively, the "Expression Response" of a cell population). As used herein, the Expression Response of a cell population is said to be "altered" if it differs from the Expression Response of a control cell population. Differences may include changes in level, timing or stability of expression in one or more of the sequences being monitored. Such alterations may occur, for example, across a temporal profile of *Myxococcus xanthus* growth, or in response to various treatments of a population of *Myxococcus xanthus* cells, such as changes to growth substrate or temperature. To determine whether a Expression Response is altered, the Expression Response manifested by the cell population is compared with that of a similar cell population which is not being grown under the treatment in question. As will be appreciated, it is not necessary to re-determine the Expression Response of the cell or tissue sample of similar cell population which is not being grown under the treatment in question each time such a comparison is made; rather, the Expression Response of a particular organism may be compared with previously obtained values of a control cell population.

Of particular interest is the use of nucleic acid molecules of the present invention to monitor gene expression in *Myxococcus* by transcriptional profiling. For example, a microarray-based method for high-throughput monitoring of gene expression may be utilized to measure gene-specific hybridization targets. This 'chip'-based approach involves using microarrays of nucleic acid molecules as gene-specific hybridization targets to quantitatively measure transcription of the corresponding genes. Every sequence in a large population, such as one representing the entire genome of *Myxococcus xanthus*, can be queried at the same time.

Transcription analysis conducted in such a manner will allow for valuable discoveries related to the *Myxococcus xanthus* genome. For example, coordinately regulated genes may be identified and such information in combination with identification of gene function by comparison to sequence of known related genes will allow for development of a stoichiometric metabolic model of the *Myxococcus xanthus* bacterium. Genes can be identified in the bacterial genome and such knowledge leads to the identification of a significant fraction of the enzymes available for cellular metabolism. The collection of enzymes can be organized into a metabolic (or stoichiometric) model for the organism (Selkov et al., *Nucleic Acids Res.* 26(1):43–45 (1998)) to provide insight and hypotheses required to direct effective metabolic engineering.

Thus, the provided MYXUs, which represent substantially all of the genes in *M. xanthus* genome, will find use in transcription profiling work to analyze genes and pathways, including identification of branch points, rate limiting steps, and changes in response to stimuli. Of particular interest is the use of such methods to identify functions for uncharacterized genes and/or genome regions, identify and characterize previously unknown genes, analyze metabolic pathways, such as those involved in carbon utilization and intercell communications. For example, if unknown genes are disrupted or overexpressed, transcription profiling can be carried out to understand effects of the genetic modification.

Several methods have been described for fabricating microarrays of nucleic acid molecules and using such microarrays in detecting nucleic acid sequences. For instance, microarrays can be fabricated by spotting nucleic acid molecules, e.g. genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Useful substrates for arrays include nylon, glass and silicon. See, for instance, U.S. Pat. Nos. 5,202,231; 5,445,934; 5,525,464; 5,700,637; 5,744,305; 5,800,992, the entirety of the disclosures of all of which are incorporated herein by reference. It is noted that additional methods for generating arrays of nucleic acids may be developed which may utilize different substrates and provide for arrays of higher nucleic acid densities. Such methods may be applied equally with the nucleic acid molecules of the present invention as do the methods currently available.

Sequences can be efficiently analyzed by hybridization to a large set of oligonucleotides or cDNA molecules representing a large portion of the genes in a genome. An array consisting of oligonucleotides or longer DNA molecules, such as cDNAs or amplified gene regions, can be used to determine the identity of a target sequence, measure its amount, and detect differences between the target and a reference sequence. Nucleic acid molecule microarrays may also be screened with molecules or fragments thereof to determine nucleic acid molecules that specifically bind molecules or fragments thereof.

The microarray approach may also be used with the *Myxococcus* polypeptides of the present invention (U.S. Pat. Nos. 5,445,934; 5,143,854; 5,079,600; 4,923,901, all of which are herein incorporated by reference in their entirety). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides.

It is understood that one or more of the molecules of the present invention, preferably one or more of the nucleic acid molecules or protein molecules or fragments thereof of the present invention may be utilized in a microarray based method. In a preferred embodiment of the present invention, one or more of the *M. xanthus* nucleic acid molecules or protein molecules or fragments thereof of the present invention may be utilized in a microarray based method. A particularly preferred microarray embodiment of the present invention is a microarray comprising *M. xanthus* nucleic acid molecules encoding genes or fragments thereof that are homologs of known genes or nucleic acid molecules. A further preferred microarray embodiment of the present invention is a microarray comprising *M. xanthus* nucleic acid molecules having genes or fragments thereof that are homologs of known genes and *M. xanthus* nucleic acid molecules that comprise genes or fragment thereof that elicit only limited or no matches to known genes.

The microarrays of the present invention comprise at least 50 nucleic acid molecules that specifically hybridize under high stringency to at least 50 nucleic acid molecules encoding *M. xanthus* proteins or fragments thereof. In a more preferred embodiment, the microarrays of the present invention comprise at least 100 nucleic acid molecules that specifically hybridize under high stringency to at least 100 nucleic acid molecules that encode a *M. xanthus* protein or fragment thereof. In an even more preferred embodiment, the microarrays of the present invention comprise at least 1000 nucleic acid molecules that specifically hybridize under high stringency to at least 1000 nucleic acid molecules that encode a *M. xanthus* protein or fragment thereof. In a further even more preferred embodiment, the microarrays of the present invention comprise at least 5000 nucleic acid molecules that specifically hybridize under high stringency to at least 5000 nucleic acid molecules that encode a *M. xanthus* protein or fragment thereof. It is, of course, understood that the sets or 50, 100, 1000 or 5000 nucleic acid molecules for the most part comprise non-identical nucleic acid molecules. While it is understood that a single nucleic acid molecule may encode more than one protein or fragment thereof, in a preferred embodiment, at least 50%, preferably at least 70%, more preferably at least 80%, even more preferably at least 90% of the nucleic acid molecules present on the microarrays encode one protein homolog or fragment thereof.

While it is understood that a single nucleic acid molecule may encode more than one protein or fragment thereof, in a preferred embodiment, at least 50%, preferably at least 70%, more preferably at least 80%, even more preferably at least 90% of the nucleic acid molecules present on the microarrays encode one protein homolog or fragment thereof. In a preferred embodiment, the microarrays of the present invention comprise nucleic acid molecules that specifically hybridize under high stringency to MYXUs selected from the group having SEQ ID NO: 1850 through SEQ ID NO: 9691 or fragments thereof or complements of either. In a more preferred embodiment, the microarrays of the present invention comprise at least about 50, 100, 250, 500, 100, 2,000, 2,500 or 5,000 nucleic acid molecules that specifically hybridize under high stringency to a corresponding number of MYXUs selected from the group having SEQ ID NO: 1850 through SEQ ID NO: 9691 or fragments thereof or complements of either. Alternatively, such microarrays can comprise oligonucletides, primers or polypeptides corresponding to the MYXUs, particularly the polypeptides provided herein as SEQ ID NO: 9692 through SEQ ID NO: 16825.

Nucleic acid molecules of the present invention may also be used in site-directed mutagenesis. Site-directed mutagenesis may be utilized to modify nucleic acid sequences, particularly as it is a technique that allows one or more of the amino acids encoded by a nucleic acid molecule to be replaced by other amino acids, e.g., threonine replaced by methionine or a larger segment replaced by a marker. It is understood that mutants with more than one altered nucleotide can be constructed using techniques well known to those skilled in the art such as isolating restriction fragments and ligating such fragments into a vector. Methods for site-directed mutagenesis include (a) homologous recombination, (b) cassette mutagenesis, (c) primer extension and (d) methods based on PCR. See also U.S. Pat. Nos. 5,880,275, 5,380,831, and 5,625,136. Any of the nucleic acid molecules of the present invention may either be modified by site-directed mutagenesis or used, for example, as nucleic acid molecules for targeting other nucleic acid molecules for modification.

Collections of Nucleic Acid Molecules and Polypeptides

Another aspect of this invention considers collections of nucleic acid molecules and/or polypeptide molecules associated with the MYXUs. The collections can include from about 50 non-identical members or more, e.g. at least about 100 or 250 or higher, more preferably at least about 500 or 1000, most preferably at least 2000 or higher, up to about 4000, or 6000 or even higher, say about 7500, or more non-identical members. Preferred collections of nucleic acid molecules, for example, can be selected from the following groups of MYXUs whose sequences are provided as SEQ ID NO:1850 through SEQ ID NO:9691:

All MYXUs;

MYXUs having a reported Bit score of at least 100;

MYXUs having a reported GeneMark probability score of at least 0.60;

MYXUs having a reported Bit score of at least 100 and a reported GeneMark probability score of at least 0.60;

MYXUs having a reported Bit score of at least 150;

MYXUs having a reported GeneMark probability score of at least 0.75;

MYXUs having a reported Bit score of at least 150 and a reported GeneMark probability score of at least 0.75.

Other preferred nucleic acid collections include any of the above groups but where such groups also include fragments of such sequences.

Collections of polypeptide molecules are also considered in the present invention, including collections of all peptides listed in Table 3 and whose sequences are provided herein as SEQ ID NO: 9692 through SEQ ID NO:16825. Other preferred collections of polypeptides include:

Polypeptides encoded by MYXUs having a reported Bit score of at least 100;

Polypeptides encoded by MYXUs having a reported GeneMark probability score of at least 0.60;

Polypeptides encoded by MYXUs having a reported Bit score of at least 100 and a reported GeneMark probability score of at least 0.60;

Polypeptides encoded by MYXUs having a reported Bit score of at least 150;

Polypeptides encoded by MYXUs having a reported GeneMark probability score of at least 0.75;

Polypeptides encoded by MYXUs having a reported Bit score of at least 150 and a reported GeneMark probability score of at least 0.75.

Another aspect of this invention provides genes, nucleic acid molecules, polypeptides and/or primers in a substantially pure form. For instance, by use of primers specific to nucleic acid sequences of this invention, nucleic acid molecules, such as MYXUs, can be produced in substantially pure form by PCR.

Another aspect of this invention is to provide methods for determining gene expression, e.g. identifying homologous genes expressed by non-*M. xanthus* organisms. Such methods comprise collecting mRNA from tissue of such organisms, using the mRNA as a template for producing a quantity of labeled nucleic acid, and contacting the labeled nucleic acid molecule with a collection of purified nucleic acid molecules, e.g. on a microarray.

Computer Media

One or more of the nucleotide sequence provided in SEQ ID NO: 1, through SEQ ID NO: 9691 or complements or fragments of either, or the protein sequences provided as SEQ ID NO: 9692 through SEQ ID NO: 16825, or fragments thereof, can be "provided" in a variety of media to facilitate use. Such a medium can also provide a subset thereof in a form that allows a skilled artisan to examine the sequences. In one application of this embodiment, a nucleotide or protein sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; optical scanner readable medium such as printed paper, and hybrids of these categories such as magnetic/optical storage media. A skilled artisan can readily appreciate how any of the presently known computer readable mediums can be used to create a manufacture comprising computer readable medium having recorded thereon a nucleotide and/or protein sequence of the present invention.

As used herein, "recorded" refers to a process for storing information on computer readable medium. A skilled artisan can readily adopt any of the presently known methods for recording information on computer readable medium to generate media comprising the nucleotide and/or protein sequence information of the present invention. In addition, a variety of data processor programs and formats can be used to store the sequence information of the present invention on computer readable medium. The sequence information can be represented in a word processing text file, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide and/or protein sequence information of the present invention.

By providing one or more of nucleotide and/or protein sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST and/or BLAZE search algorithms on a Sybase system can be used to identify open reading frames (ORFs) within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means, and data storage means used to analyze the nucleotide and/or protein sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide and/or protein sequence information of the present invention, or a memory access means which can access manufactures having recorded thereon the sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available can be used in the computer-based systems of the present invention. Examples of such software include, but are not limited to, MacPattern (EMBL), BLASTIN and BLASTIX (NCBIA). One of the available algorithms or implementing software packages for conducting homology searches can be adapted for use in the present computer-based systems.

The most preferred sequence length of a target sequence is from about 30 to 300 nucleotide residues or from about 10 to 100 amino acids. However, it is well recognized that during searches for commercially important fragments of the molecules of the present invention, such as sequence fragments involved in gene expression and protein processing, the target sequence may be of shorter length.

As used herein, "a target structural motif," or "target motif," refers to any rationally selected sequence or combination of sequences in which the sequences are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention identified using a search means as described above, and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences that contain various amounts of the target sequence or target motif and identifies the degree of homology contained in the identified fragment.

Having now generally described the invention, the same will be more readily understood through reference to the following examples that are provided by way of illustration, and are not intended to be limiting of the present invention, unless specified.

EXAMPLES

Example 1

Generation and Assembly of *M. xanthus* Genome Sequence

This example serves to illustrate the generation of the 1849 nucleic acid sequences listed in Table 1 as contigs having SEQ ID NO: 1 through SEQ ID NO: 1849. Approximately 58000 genomic nucleotide sequence traces were derived from a double stranded plasmid library prepared from *Myxococcus xanthus* strain DK1622. The two basic methods for the DNA sequencing are the chain termination method of Sanger et al., *Proc. Natl. Acad. Sci. (U.S.A.)* 74:5463–5467 (1977) and the chemical degradation method of Maxam and Gilbert, *Proc. Natl. Acad. Sci. (U.S.A.)* 74:560–564 (1977) using automated fluorescence-based sequencing as reported by Craxton, *Method*, 2:20–26 (1991); Ju et al., *Proc. Natl. Acad. Sci. (U.S.A.)* 92:4347–4351 (1995); and Tabor and Richardson, *Proc. Natl. Acad Sci. (U.S.A.)* 92:6339–6343 (1995) and high speed capillary gel electrophoresis, e.g. as disclosed by Swerdlow and Gesteland, *Nucleic Acids Res.* 18:1415–1419 (1990); Smith, *Nature* 349:812–813 (1991); Luckey et al., *Methods Enzymol.* 218:154–172 (1993); Lu et al., *J. Chromatog. A.* 680:497–501 (1994); Carson et al., *Anal. Chem* 65:3219–3226 (1993); Huang et al., *Anal. Chem.* 64:2149–2154 (1992); Kheterpal et al., *Electrophoresis* 17:1852–1859 (1996); Quesada and Zhang, *Electrophoresis* 17:1841–1851 (1996); Baba, *Yakugaku Zasshi* 117:265–281 (1997). For instance, genomic nucleotide sequence traces are generated using a 377 or 3700 DNA Sequencer (Perkin-Elmer Corp., Applied Biosystems Div., Foster City, Calif.) allowing for rapid electrophoresis and data collection. With these types of automated systems, fluorescent dye-labeled sequence reaction products are detected and chromatograms are subsequently viewed, stored in a computer and analyzed using corresponding apparatus-related software programs. These methods are known to those of skill in the art and have been described and reviewed (Birren et al., *Genome Analysis: Analyzing DNA,*1, Cold Spring Harbor, N.Y.).

Over 58,000 quality genomic sequence traces are assembled generally as follows:

(a) all traces are "vector-trimmed" i.e., 5' and 3' vector and linker sequences are removed;

(b) a PHRAP assembly is run using default assembly parameters;

(c) Contigs and singletons files and their corresponding quality files are united to create "islands"; and (d) the final set of 1849 nucleic acid sequences (identified as SEQ ID NO. 1 through SEQ ID NO:1849) are run through the annotation and gene selection processes as described in Example 2. Contigs in SEQ ID NO. 1 through SEQ ID NO:1849 are recognized as those sequences whose designations begin with MYX10C. Singleton sequences are recognized as those having designations that begin with MYX10S.

A list of the contig and singleton sequences of this invention is provided in Table 1 and the nucleic acid sequences provided as SEQ ID NO: 1 through SEQ ID NO: 1849.

Example 2

Identification of *Myxococcus xanthus* Genes

This example illustrates the identification of genes within the 1849 islands assembled as described in Example 1. The genes and partial genes embedded in SEQ ID NO. 1 through SEQ ID NO:1849 are identified through a series of informatic analyses. Homology-based searches were used to detect conserved sequences during comparisons of DNA sequences or hypothetically translated protein sequences to public and/or proprietary DNA and protein databases. Existence of an *Myxococcus xanthus* gene is inferred if significant sequence similarity extends over the majority of the target gene. The homology-based method used to define the *Myxococcus xanthus* gene set was BLASTX. For a description of BLASTX see Coulson, *Trends in Biotechnology* 12:76–80 (1994) and Birren et al., *Genome Analysis,* 1:543–559 (1997). BLASTX takes a nucleotide sequence, translates it in three forward reading frames and three reverse complement reading frames, and then compares the six translations against a protein sequence database (e.g. the non-redundant protein (i.e., nr-aa) database maintained by the National Center for Biotechnology Information as part of GenBank and available at the web site: http://www.ncbi.nlm.nih.gov). BLASTX is run with the *Myxococcus xanthus* contigs and singletons represented by SEQ ID NO: 1 through SEQ ID NO: 1849 as queries against the GenBank non-redundant protein data library identified as "nr-aa". To identify genes solely by BLASTX, the minimum BLASTX E value is set at 1E-08.

Since homology-based methods may overlook genes unique to *Myxococcus xanthus*, for which homologous nucleic acid molecules have not yet been identified in databases, gene prediction programs are also used. Additional *M. xanthus* genes with no known homologs under the above BLASTX analysis parameters were predicted using the GeneMark sequence analysis program (Borodovsky et al. *Computers & Chemistry* 17:123–133 (1993)). GeneMark is available from Gene Pro (Atlanta, Ga.) or from Georgia Tech University (e.g. at the web site (see http://genemark.biology.gatech.edu/GeneMark for details). GeneMark calculates the probability of a gene being present based on the presence of a gene-like 'grammer' in the target DNA sequence (i.e., start and stop signals, and a significant open reading frame) and statistical analyses of protein-coding potential through biases in putative codon usage. GeneMark uses inhomogeneous Markov chain models derived from comparisons of known coding and non-coding sequences to predict the presence of protein-coding regions. The GeneMark program is "trained" with *M. xanthus* characteristics. Predicting full-length genes is comprised by point mutations in the unfinished contigs, as well as by the short length of contigs relative to the typical length of a gene. Due to the errors found in the full-length gene predictions by GeneMark, inclusion of GeneMark-predicted genes is limited to those genes and ORFs of partial genes whose probabilities are above the threshold of p.>0.5.

The results of the homology based and predictive analysis methods were merged into a single set of predicted coding regions, and their most probable translation. In setting criteria for confidence of gene prediction, a "high" BLASTX match as used herein means a match having a BLASTX Bit Score as provided in Table 1 of greater than 150; a medium BLASTX Bit Score is 100 to 150; and a low BLASTX Bit Score is less than 100. "Bits" refers to information content, and the score in the "Bits" column indicates the amount of information in the hit. A higher BLASTX Bit Score indicates a better match. Low complexity matches (which can generate high BLAST scores if they match over long stretches with other low quality data) are inherently low information content, and hence do not generate high Bit Scores. A "high" GeneMark Probability Score as used herein means a score as provided in Table 1 of greater than 0.75; a medium GeneMark Probability Score is 0.60 to 0.75; and a low GeneMark Probability Score is less than 0.60. Confidence in accuracy decreases with decreasing BLASTX Bit Score or GeneMark Probability Score. For example, medium confidence is associated with BLASTX Bit Scores of from 100–150, as well as with GeneMark Probability Scores of 0.60–0.75. Confidence increases if a predicted gene has high or medium scores by both BLASTX and GeneMark analysis, as opposed to just having been identified by one or the other types of analysis. Thus, the order of confidence for the MYXUs is generally as follows:

| Confidence | BLASTX Bit Score | GeneMark Probability Score |
|---|---|---|
| high | high (>150) | high (>0.75) |
|  | high | — |
|  | — | high |
| medium | medium (100–150) | medium (0.6–0.75) |
|  | medium | low (<0.6) |
|  | low (<100) | medium |
| low | low | low |

In Table 1, protein encoding regions in the *Myxococcus* nucleic acid molecules of the present invention are identified and results of the BLAST and GeneMark analyses are provided.

A list of the predicted proteins is provided in Table 1 and the amino acid sequences for the *Myxococcus* proteins are provided as SEQ ID NO:9692 through SEQ ID NO: 16825. Predicted proteins are provided where predicted by both BLASTX and GeneMark and for most genes identified solely by GeneMark. The predicted amino acid sequences are the most probable translations for the identified start and stop signals, and the biases in codon usage seen in *Myxococcus* genes.

Legend for Table 1

Seq num

Provides the SEQ ID NO for the listed sequences.

Seq id

The arbitrary identification assigned to each contig or singleton of genomic sequence for SEQ ID NO: 1 through SEQ ID NO:1849 where the "Seq id" for a contig name begins with MYX10C and a singleton name begins with MYX10S. The arbitrarily identification assigned for each MYXU (*Myxococcus xanthus* unigene) for SEQ ID NO: 1850 through SEQ ID NO: 9691 where the "Seq id" is MYX12U_xxxx. The identification assigned to each translated protein of the MYXUs for SEQ ID NO:9692 through SEQ ID NO:16825, where the "Seq id" contains the identification for the corresponding MYXU followed by the designation "prot", for example MYX12U_6967_prot.

Position

Indicates contigs or singletons from which the MYXUs are identified and the location of the MYXU within the contig or singleton. In cases where the first numeral is higher than its corresponding second numeral, the *A. tumefaciens* protein or fragment thereof is encoded by the complement of the sequence set forth in the sequence listing.

Ncbi gi

Refers to National Center for Biotechnology Information GenBank Identifier number that is the best match for a given contig or singleton region from which the protein encoding region was identified.

Bits

Bit score for BLAST match

Blast Expect

The entries in the "Blast Expect" column refer to the probability that matches occur by chance.

% id

The entries in the "% id" column of the table refer to the percentage of identically matched nucleotides (or residues) that exist along the length of that portion of the sequences which is aligned by the BLAST comparison.

% cvrg

The "% cvrg" is the percent of hit sequence length that matches to the query sequence in the match generated using BLAST (% cvrg=(match length/hit total length)× 100).

GeneMark prob

The "GeneMark_prob" is a measure of the likelihood that a region of DNA codes for a protein sequence as determined by the GeneMark gene-prediction program.

Description

A description of the database entry referenced in the "NCBI gi" column. Sequences were analyzed by BLASTX against the non-redundant protein database maintained by NCBI, and a description of the top hit is provided.

Example 3
Design and Preparation of Oligonucleotide Primers

This example serves to illustrate the design of primers of this invention that are useful, for instance, for initiating synthesis of nucleic acid molecules of this invention, specifically substantial parts of certain MYXUs of this invention. Such primers may be designed with the program Primer3 (obtained from the MIT-Whitehead Genome Center) with a "perl-oracle" wrapper. The criteria applied to design a primer include:

Primer annealing temperature (minimum 65° C., optimum 70° C., maximum 75° C.)

Primer length (minimum 18 bp, optimum 20 bp, maximum 28 bp)

G+C content (minimum 20%, maximum 80%)

Position of the primer relative to the gene

Length of the amplified region (200 to 1000 bp, optimum 500 bp)

PHRED quality score of the gene template (minimum of 20)

Whether the gene was defined from one or two contigs

Maximum mismatch=12.0 (weighted score from Primer3 program)

Pair Max Misprime=24.0 (weighted score from Primer3 program)

Maximum N's=0

Maximum poly-X=5

The primary goal of the design process is the creation of groups of primer pairs with a common annealing temperature ($T_m$). When the program can identify a primer pair for any gene that fit the criteria, the gene can be removed from the bin of genes needing primer design. Genes remaining in the bin are subjected to additional rounds of primer-picking, with the gradual and simultaneous relaxation of the criteria (i.e., lowering the annealing temperature, increasing the size of the window where primers could be predicted, expanding the range of permitted size and G+C content, removing the need for a G/C clamp), until a sufficient number of primers are picked for the MYXUs of this invention.

After the *M. xanthus* specific portion of the primers is selected, an additional common primer tail sequence (universal primer) can be added to the 5' ends so that subsequent reamplifications of any primer pair can be done with a single set of primers. In addition, the primer tail sequences may contain restriction digestion sites, preferably for 8 bp recognition restriction enzymes (i.e., NotI and SgfI) and 6 bp cutters (i.e., EcoRI and XhoI) to facilitate cloning of MYXUs into vectors.

Example 4
Discovery of Polyketide Synthase Encoding Genes in *Myxococcus xanthus*

*Myxococcus xanthus* genes encoding polyketide synthases were identified by a series of predictive and homology based methods. Known polyketide synthase gene and protein sequences were used in homology based identification. A list of genes encoding, polyketide synthases discovered in *Myxococcus xanthus* is provided in Table 2 below.

TABLE 2

| GeneName | SEQ ID | SEQ NUM | Organism |
| --- | --- | --- | --- |
| (AE005305) beta-ketoacyl-[acyl carrier protein] synthase | MYX12U_2293 | 4142 | *Escherichia coli* O157:H7 |
| (AE005305) beta-ketoacyl-[acyl carrier protein] synthase | MYX12U_2298 | 4147 | *Escherichia coli* O157:H7 |
| (AF188287) MtaB | MYX12U_4398 | 6246 | *Stigmatella aurantiaca* |
| (AF188287) MtaB | MYX12U_5330 | 7178 | *Stigmatella aurantiaca* |
| (AF188287) MtaD | MYX12U_2103 | 3952 | *Stigmatella aurantiaca* |
| (AF188287) MtaD | MYX12U_2104 | 3953 | *Stigmatella aurantiaca* |
| (AF188287) MtaD | MYX12U_4706 | 6554 | *Stigmatella aurantiaca* |
| (AF188287) MtaD | MYX12U_5343 | 7191 | *Stigmatella aurantiaca* |
| (AF188287) MtaE | MYX12U_4908 | 6756 | *Stigmatella aurantiaca* |
| (AF188287) MtaF | MYX12U_1043 | 2892 | *Stigmatella aurantiaca* |
| (AF188287) MtaG | MYX12U_1440 | 3289 | *Stigmatella aurantiaca* |
| (AF188287) MtaG | MYX12U_1442 | 3291 | *Stigmatella aurantiaca* |
| (AF188287) MtaG | MYX12U_4799 | 6647 | *Stigmatella aurantiaca* |
| (AF204805) NosA | MYX12U_1172 | 3021 | *Nostoc* sp. GSV224 |
| (AF204805) NosA | MYX12U_1195 | 3044 | *Nostoc* sp. GSV224 |
| (AF204805) NosA | MYX12U_1266 | 3115 | *Nostoc* sp. GSV224 |

TABLE 2-continued

| GeneName | SEQ ID | SEQ NUM | Organism |
|---|---|---|---|
| (AF204805) NosA | MYX12U_3988 | 5836 | *Nostoc* sp. GSV224 |
| (AF204805) NosA | MYX12U_4232 | 6080 | *Nostoc* sp. GSV224 |
| (AF204805) NosA | MYX12U_4340 | 6188 | *Nostoc* sp. GSV224 |
| (AF204805) NosA | MYX12U_4877 | 6725 | *Nostoc* sp. GSV224 |
| (AF204805) NosA | MYX12U_4909 | 6757 | *Nostoc* sp. GSV224 |
| (AF204805) NosA | MYX12U_5006 | 6854 | *Nostoc* sp. GSV224 |
| (AF204805) NosA | MYX12U_7749 | 9597 | *Nostoc* sp. GSV224 |
| NosA | MYX12U_6066 | 7914 | *Nostoc* sp. GSV224 |
| NosB | MYX12U_4852 | 6700 | *Nostoc* sp. GSV224 |
| NosB | MYX12U_7008 | 8856 | *Nostoc* sp. GSV224 |
| NosB | MYX12U_7307 | 9155 | *Nostoc* sp. GSV224 |
| (AF204805) NosB | MYX12U_1520 | 3369 | *Nostoc* sp. GSV224 |
| (AF204805) NosB | MYX12U_391 | 2240 | *Nostoc* sp. GSV224 |
| (AF204805) NosB | MYX12U_3994 | 5842 | *Nostoc* sp. GSV224 |
| (AF204805) NosB | MYX12U_4068 | 5916 | *Nostoc* sp. GSV224 |
| (AF204805) NosB | MYX12U_7308 | 9156 | *Nostoc* sp. GSV224 |
| (AF204805) NosC | MYX12U_4894 | 6742 | *Nostoc* sp. GSV224 |
| (AF204805) NosC | MYX12U_5491 | 7339 | *Nostoc* sp. GSV224 |
| (AF204805) NosC | MYX12U_5524 | 7372 | *Nostoc* sp. GSV224 |
| (AF204805) NosC | MYX12U_6349 | 8197 | *Nostoc* sp. GSV224 |
| (AF204805) NosC | MYX12U_6959 | 8807 | *Nostoc* sp. GSV224 |
| (AF204805) NosC | MYX12U_6961 | 8809 | *Nostoc* sp. GSV224 |
| (AF204805) NosD | MYX12U_4568 | 6416 | *Nostoc* sp. GSV224 |
| (AF204805) NosD | MYX12U_4892 | 6740 | *Nostoc* sp. GSV224 |
| (AF204805) NosD | MYX12U_4897 | 6745 | *Nostoc* sp. GSV224 |
| (AF204805) NosD | MYX12U_5176 | 7024 | *Nostoc* sp. GSV224 |
| (AF204805) NosD | MYX12U_5237 | 7085 | *Nostoc* sp. GSV224 |
| (AF210249) peptide synthetase NRPS5A-4-3 | MYX12U_1175 | 3024 | *Streptomyces verticillus* |
| (AF210843) nonribosomal peptide synthetase | MYX12U_151 | 2000 | *Sorangium cellulosum* |
| (AF210843) polyketide synthase | MYX12U_4260 | 6108 | *Sorangium cellulosum* |
| (AF210843) polyketide synthase | MYX12U_6135 | 7983 | *Sorangium cellulosum* |
| (AF210843) polyketide synthase | MYX12U_6506 | 8354 | *Sorangium cellulosum* |
| (AF210843) polyketide synthase | MYX12U_7140 | 8988 | *Sorangium cellulosum* |
| (AF217189) EpoC | MYX12U_4619 | 6467 | *Sorangium cellulosum* |
| (AF217189) EpoC | MYX12U_5715 | 7563 | *Sorangium cellulosum* |
| (AF217189) epoD | MYX12U_6046 | 7894 | *Sorangium cellulosum* |
| (AF217189) epoD | MYX12U_6520 | 8368 | *Sorangium cellulosum* |
| (AF217189) epoD | MYX12U_6564 | 8412 | *Sorangium cellulosum* |
| (AF217189) EpoF | MYX12U_4758 | 6606 | *Sorangium cellulosum* |
| (AF299336) MxcG | MYX12U_4896 | 6744 | *Stigmatella aurantiaca* |
| (AF322013) ID930 | MYX12U_6264 | 8112 | *Bradyrhizobium japonicum* |
| (AJ006977) Ta1 | MYX12U_3797 | 5645 | *Myxococcus xanthus* |
| (AJ006977) Ta1 | MYX12U_3798 | 5646 | *Myxococcus xanthus* |
| (AJ006977) Ta1 | MYX12U_3801 | 5649 | *Myxococcus xanthus* |
| (AJ269505) peptide synthetase | MYX12U_2593 | 4442 | *Anabaena* sp. 90 |
| (AJ269505) peptide synthetase | MYX12U_4152 | 6000 | *Anabaena* sp. 90 |
| (AJ269505) peptide synthetase | MYX12U_5002 | 6850 | *Anabaena* sp. 90 |
| (AJ310530) siderophore non-ribosomal peptide synthetase | MYX12U_6276 | 8124 | *Pseudomonas putida* |
| aklaviketone reductase | MYX12U_3952 | 5800 | *Mycobacterium tuberculosis* |
| pksd | MYX12U_3807 | 5655 | *Bacillus subtilis* |
| polyketide synthase ORF2 | MYX12U_3998 | 5846 | *Bacillus subtilis* |
| POLYKETIDE SYNTHASE PKSL (PKS) | MYX12U_4009 | 5857 | *Bacillus subtilis* |
| POLYKETIDE SYNTHASE PKSM | MYX12U_5033 | 6881 | *Bacillus subtilis* |
| polyketide synthetase pksP | MYX12U_7099 | 8947 | *Bacillus subtilis* |
| polyketide synthetase pksP | MYX12U_7100 | 8948 | *Bacillus subtilis* |
| polyketide synthetase pksP | MYX12U_7302 | 9150 | *Bacillus subtilis* |
| acrA1 protein - *Mycobacterium tuberculosis* (strain H37RV) | MYX12U_6211 | 8059 | *Mycobacterium tuberculosis* |
| ketoacyl reductase - *Deinococcus radiodurans* (strain R1) | MYX12U_1777 | 3626 | *Deinococcus radiodurans* |
| multi-domain beta keto-acyl synthase | MYX12U_3095 | 4944 | *Streptomyces coelicolor* A3(2) |
| non-ribosomal peptide synthetase PA2402 | MYX12U_536 | 2385 | *Pseudomonas aeruginosa* |
| non-ribosomal peptide synthetase PA2402 | MYX12U_537 | 2386 | *Pseudomonas aeruginosa* |
| non-ribosomal peptide synthetase PA2402 | MYX12U_538 | 2387 | *Pseudomonas aeruginosa* |
| non-ribosomal peptide synthetase PA2424 | MYX12U_4962 | 6810 | *Pseudomonas aeruginosa* |
| saframycin Mx1 synthetase A | MYX12U_4567 | 6415 | *Myxococcus xanthus* |
| saframycin Mx1 synthetase A | MYX12U_4826 | 6674 | *Myxococcus xanthus* |
| saframycin Mx1 synthetase B | MYX12U_2812 | 4661 | *Myxococcus xanthus* |
| saframycin Mx1 synthetase B | MYX12U_3575 | 5424 | *Myxococcus xanthus* |
| saframycin Mx1 synthetase B | MYX12U_4754 | 6602 | *Myxococcus xanthus* |
| saframycin Mx1 synthetase B | MYX12U_4961 | 6809 | *Myxococcus xanthus* |

TABLE 2-continued

| GeneName | SEQ ID | SEQ NUM | Organism |
|---|---|---|---|
| saframycin Mx1 synthetase B | MYX12U_662 | 2511 | *Myxococcus xanthus* |
| saframycin Mx1 synthetase B | MYX12U_730 | 2579 | *Myxococcus xanthus* |
| saframycin Mx1 synthetase B | MYX12U_736 | 2585 | *Myxococcus xanthus* |
| syringomycin synthetase | MYX12U_3155 | 5004 | *Pseudomonas syringae* pv. *syringae* |
| TYROCDINE SYNTHETASE III | MYX12U_1929 | 3778 | *Brevibacillus brevis* |

In Tables 2–4, GeneName corresponds to the name of the homolog gene used to assign function to the listed *Myxococcus* gene. SEQ ID lists the MYXU number from Table 1 for each gene. SEQ NUM provides the SEQ ID NO for each gene. Organism indicates the organism encoding the homolog listed in the GeneName column.

Example 5

Discovery of Genes Encoding Serine/threonine Protein Kinase Proteins

*Myxococcus xanthus* genes encoding serine/threonine protein kinase proteins were identified by a series of predictive and homology based methods. Known serine/threonine protein kinase gene and protein sequences were used in homology based identification. A list of genes encoding serine/threonine protein kinase proteins discovered in *Myxococcus xanthus* is provided in Table 3 below.

TABLE 3

| GeneName | SEQ ID | SEQ NUM | Organism |
|---|---|---|---|
| (AF159691) serine/threonine kinase PKN8 | MYX12U_1090 | 2939 | *Myxococcus xanthus* |
| (AF116463) regulatory protein Wd1A | MYX12U_1171 | 3020 | *Streptomyces lincolnensis* |
| (AF163841) serine/threonine protein kinase | MYX12U_1240 | 3089 | *Myxococcus xanthus* |
| (AF163841) serine/threonine protein kinase | MYX12U_1244 | 3093 | *Myxococcus xanthus* |
| (AF159689) serine/threonine kinase PKN3 | MYX12U_1371 | 3220 | *Myxococcus xanthus* |
| (AL358672) serine/threonine-protein kinase. | MYX12U_1392 | 3241 | *Streptomyces coelicolor* A3(2) |
| (AF159693) serine/threonine kinase PKN13 | MYX12U_1430 | 3279 | *Myxococcus xanthus* |
| (AF163841) serine/threonine protein kinase | MYX12U_1469 | 3318 | *Myxococcus xanthus* |
| (AF159691) serine/threonine kinase PKN8 | MYX12U_156 | 2005 | *Myxococcus xanthus* |
| (AF159693) serine/threonine kinase PKN13 | MYX12U_1588 | 3437 | *Myxococcus xanthus* |
| (AF159691) serine/threonine kinase PKN8 | MYX12U_1621 | 3470 | *Myxococcus xanthus* |
| (AF159691) serine/threonine kinase PKN8 | MYX12U_1735 | 3584 | *Myxococcus xanthus* |
| SERINE/THREONINE-PROTEIN KINASE PKN1 | MYX12U_1886 | 3735 | *Myxococcus xanthus* |
| SERINE/THREONINE-PROTEIN KINASE PKNB | MYX12U_1894 | 3743 | *Mycobacterium tuberculosis* |
| SERINE/THREONINE-PROTEIN KINASE PKN6 | MYX12U_2020 | 3869 | *Myxococcus xanthus* |
| (AF159689) serine/threonine kinase PKN3 | MYX12U_209 | 2058 | *Myxococcus xanthus* |
| (AF159690) serine/threonine kinase PKN7 | MYX12U_2165 | 4014 | *Myxococcus xanthus* |
| (AF163841) serine/threonine protein kinase | MYX12U_2208 | 4057 | *Myxococcus xanthus* |
| serine/threonine kinase | MYX12U_2237 | 4086 | |
| (AF159691) serine/threonine kinase PKN8 | MYX12U_2319 | 4168 | *Myxococcus xanthus* |
| serine/threonine kinase | MYX12U_2332 | 4181 | |
| serine/threonine kinase | MYX12U_2432 | 4281 | |
| serine-threonine kinase Stk1 PA1671 | MYX12U_2459 | 4308 | *Pseudomonas aeruginosa* |
| (AF159690) serine/threonine kinase PKN11 | MYX12U_2478 | 4327 | *Myxococcus xanthus* |
| (AF159691) serine/threonine kinase PKN8 | MYX12U_249 | 2098 | *Myxococcus xanthus* |
| SERINE/THREONINE-PROTEIN KINASE PKN1 | MYX12U_2565 | 4414 | *Myxococcus xanthus* |
| serine/threonine kinase | MYX12U_2577 | 4426 | |
| (AF159690) serine/threonine kinase PKN11 | MYX12U_267 | 2116 | *Myxococcus xanthus* |
| (AF159691) serine/threonine kinase PKN8 | MYX12U_2771 | 4620 | *Myxococcus xanthus* |
| (AL583925) possible regulatory protein | MYX12U_2810 | 4659 | *Mycobacterium leprae* |
| (AF159693) serine/threonine kinase PKN13 | MYX12U_2824 | 4673 | *Myxococcus xanthus* |
| serine/threonine protein kinase | MYX12U_2864 | 4713 | *Streptomyces griseus* |
| (AF159690) serine/threonine kinase PKN11 | MYX12U_2913 | 4762 | *Myxococcus xanthus* |

TABLE 3-continued

| GeneName | SEQ ID | SEQ NUM | Organism |
|---|---|---|---|
| (AF159690) serine/threonine kinase PKN11 | MYX12U_2916 | 4765 | Myxococcus xanthus |
| serine/threonine kinase | MYX12U_2986 | 4835 | |
| protein kinase-like protein | MYX12U_2997 | 4846 | Streptomyces coelicolor A3(2) |
| (AF159691) serine/threonine kinase PKN8 | MYX12U_3061 | 4910 | Myxococcus xanthus |
| (AF026951) ATP-and/or GTP-binding protein | MYX12U_3109 | 4958 | Myxococcus xanthus |
| serine/threonine protein kinase | MYX12U_3418 | 5267 | Myxococcus xanthus |
| (AF159689) serine/threonine kinase PKN3 | MYX12U_3470 | 5319 | Myxococcus xanthus |
| (AC005802) L6202.3 | MYX12U_3482 | 5331 | Leishmania major |
| (AF159689) serine/threonine kinase PKN3 | MYX12U_3490 | 5339 | Myxococcus xanthus |
| (AF159689) serine/threonine kinase PKN3 | MYX12U_3523 | 5372 | Myxococcus xanthus |
| (AF159692) serine/threonine kinase PKN12 | MYX12U_3553 | 5402 | Myxococcus xanthus |
| SERINE/THREONINE-PROTEIN KINASE PKN6 | MYX12U_3566 | 5415 | Myxococcus xanthus |
| serine/threonine kinase | MYX12U_3673 | 5522 | |
| serine/threonine kinase | MYX12U_3675 | 5524 | |
| SERINE/THREONINE-PROTEIN KINASE PKN6 | MYX12U_3704 | 5553 | Myxococcus xanthus |
| probable protein serine-threonine phosphatase - Deinococcus radiodurans (strain R1) | MYX12U_3753 | 5602 | Deinococcus radiodurans |
| SERINE/THREONINE-PROTEIN KINASE PKN2 | MYX12U_3773 | 5621 | Myxococcus xanthus |
| SERINE/THREONINE-PROTEIN KINASE PKN6 | MYX12U_3853 | 5701 | Myxococcus xanthus |
| (AF159690) serine/threonine kinase PKN7 | MYX12U_3882 | 5730 | Myxococcus xanthus |
| (AF159690) serine/threonine kinase PKN7 | MYX12U_3971 | 5819 | Myxococcus xanthus |
| (AF159690) serine/threonine kinase PKN11 | MYX12U_4114 | 5962 | Myxococcus xanthus |
| SERINE/THREONINE-PROTEIN KINASE PKN2 | MYX12U_4166 | 6014 | Myxococcus xanthus |
| (AF159690) serine/threonine kinase PKN7 | MYX12U_4332 | 6180 | Myxococcus xanthus |
| (AF159691) serine/threonine kinase PKN8 | MYX12U_4494 | 6342 | Myxococcus xanthus |
| SERINE/THREONINE-PROTEIN KINASE PKN2 | MYX12U_4519 | 6367 | Myxococcus xanthus |
| (AF159692) serine/threonine kinase PKN12 | MYX12U_4581 | 6429 | Myxococcus xanthus |
| (AF159689) serine/threonine kinase PKN3 | MYX12U_471 | 2320 | Myxococcus xanthus |
| (AF159690) serine/threonine kinase PKN7 | MYX12U_473 | 2322 | Myxococcus xanthus |
| (AF159689) serine/threonine kinase PKN3 | MYX12U_4797 | 6645 | Myxococcus xanthus |
| SERINE/THREONINE-PROTEIN KINASE PKN1 | MYX12U_4837 | 6685 | Myxococcus xanthus |
| (AF159690) serine/threonine kinase PKN7 | MYX12U_4899 | 6747 | Myxococcus xanthus |
| SERINE/THREONINE-PROTEIN KINASE PKN5 | MYX12U_493 | 2342 | Myxococcus xanthus |
| SERINE/THREONINE-PROTEIN KINASE PKN6 | MYX12U_4970 | 6818 | Myxococcus xanthus |
| hypothetical protein PH0425 - Pyrococcus horikoshii | MYX12U_5054 | 6902 | Pyrococcus horikoshii |
| (AF159693) serine/threonine kinase PKN13 | MYX12U_5133 | 6981 | Myxococcus xanthus |
| SERINE/THREONINE-PROTEIN KINASE PKN1 | MYX12U_5170 | 7018 | Myxococcus xanthus |
| (AF163841) serine/threonine protein kinase | MYX12U_5314 | 7162 | Myxococcus xanthus |
| (AF159692) serine/threonine kinase PKN12 | MYX12U_5323 | 7171 | Myxococcus xanthus |
| (AF163841) serine/threonine protein kinase | MYX12U_5332 | 7180 | Myxococcus xanthus |
| (AF159690) serine/threonine kinase PKN7 | MYX12U_5594 | 7442 | Myxococcus xanthus |
| (AF159690) serine/threonine kinase PKN11 | MYX12U_5598 | 7446 | Myxococcus xanthus |
| serine/threonine kinase | MYX12U_5600 | 7448 | |
| (AF159689) serine/threonine kinase PKN3 | MYX12U_5613 | 7461 | Myxococcus xanthus |
| (AF159694) serine/threonine kinase PKN9 | MYX12U_5656 | 7504 | Myxococcus xanthus |
| (AF159690) serine/threonine kinase PKN7 | MYX12U_5659 | 7507 | Myxococcus xanthus |
| (AF159689) serine/threonine kinase PKN3 | MYX12U_5664 | 7512 | Myxococcus xanthus |
| (AF159690) serine/threonine kinase PKN7 | MYX12U_5719 | 7567 | Myxococcus xanthus |
| serine/threonine kinase | MYX12U_5728 | 7576 | |
| SERINE/THREONINE-PROTEIN KINASE PKN1 | MYX12U_5906 | 7754 | Myxococcus xanthus |
| SERINE/THREONINE-PROTEIN KINASE PKN6 | MYX12U_5926 | 7774 | Myxococcus xanthus |
| SERINE/THREONINE-PROTEIN KINASE PKN6 | MYX12U_60 | 1909 | Myxococcus xanthus |
| serine/threonine kinase | MYX12U_6146 | 7994 | |
| SERINE/THREONINE-PROTEIN KINASE PKNB | MYX12U_6292 | 8140 | Mycobacterium leprae |
| serine/threonine kinase | MYX12U_6330 | 8178 | |
| (AF159689) serine/threonine kinase PKN3 | MYX12U_6392 | 8240 | Myxococcus xanthus |
| probable multi-domain regulatory protein | MYX12U_6422 | 8270 | Streptomyces coelicolor A3(2) |
| (AF159691) serine/threonine kinase PKN8 | MYX12U_6523 | 8371 | Myxococcus xanthus |

TABLE 3-continued

| GeneName | SEQ ID | SEQ NUM | Organism |
| --- | --- | --- | --- |
| SERINE/THREONINE-PROTEIN KINASE PKN1 | MYX12U_6670 | 8518 | Myxococcus xanthus |
| serine/threonine kinase | MYX12U_669 | 2518 | |
| SERINE/THREONINE-PROTEIN KINASE PKN2 | MYX12U_67 | 1916 | Myxococcus xanthus |
| SERINE/THREONINE-PROTEIN KINASE PKN6 | MYX12U_6754 | 8602 | Myxococcus xanthus |
| (AF159691) serine/threonine kinase PKN8 | MYX12U_680 | 2529 | Myxococcus xanthus |
| (AF230361) serine/threonine kinase | MYX12U_6914 | 8762 | Nostoc sp. PCC 7120 |
| (AF159502) Pkn10 | MYX12U_7161 | 9009 | Myxococcus xanthus |
| (AF159690) serine/threonine kinase PKN7 | MYX12U_7171 | 9019 | Myxococcus xanthus |
| (AF159693) serine/threonine kinase PKN13 | MYX12U_7192 | 9040 | Myxococcus xanthus |
| (AF159690) serine/threonine kinase PKN7 | MYX12U_7258 | 9106 | Myxococcus xanthus |
| serine/threonine kinase | MYX12U_7300 | 9148 | |
| (AF159691) serine/threonine kinase PKN8 | MYX12U_7557 | 9405 | Myxococcus xanthus |
| (AF159690) serine/threonine kinase PKN7 | MYX12U_7706 | 9554 | Myxococcus xanthus |
| SERINE/THREONINE-PROTEIN KINASE PKNB | MYX12U_7778 | 9626 | Mycobacterium tuberculosis |
| SERINE/THREONINE-PROTEIN KINASE PKNB | MYX12U_7804 | 9652 | Mycobacterium tuberculosis |
| (AF159690) serine/threonine kinase PKN11 | MYX12U_7829 | 9677 | Myxococcus xanthus |
| (AF159501) pkn4 | MYX12U_862 | 2711 | Myxococcus xanthus |
| (AF159690) serine/threonine kinase PKN7 | MYX12U_950 | 2799 | Myxococcus xanthus |
| (AF159690) serine/threonine kinase PKN7 | MYX12U_981 | 2830 | Myxococcus xanthus |

Example 6
Discovery of Other *Myxococcus* Genes of Interest

*Myxococcus xanthus* genes encoding antibiotic resistance proteins, DNA modification enzymes, sigma factors and nitrate pathway proteins were identified by a series of predictive and homology based methods. Known gene and protein sequences for antibiotic resistance proteins, DNA modification enzymes, sigma factors and nitrate pathway proteins were used in homology based identification. A list of genes encoding antibiotic resistance proteins, DNA modification enzymes, such as DNA methylases and restriction enzymes, sigma factors and nitrate pathway proteins discovered in *Myxococcus xanthus* is provided in Table 4 below.

TABLE 4

| GeneName | SEQ ID | SEQ NUM | Organism |
| --- | --- | --- | --- |
| RESISTANCE MARKER GENES | | | |
| Chloramphenicol resistance protein | MYX12U_1125 | 2974 | |
| nogalamycin resistance protein snorO | MYX12U_1436 | 3285 | Streptomyces nogalater |
| probable MFS transporter PA3573; chloramphenicol and florfenicol resistance protein | MYX12U_1480 | 3329 | Pseudomonas aeruginosa |
| probable transmembrane efflux protein - Streptomyces coelicolor; chloramphenicol and florfenicol resistance protein | MYX12U_1643 | 3492 | Streptomyces coelicolor A3(2) |
| acriflavin resistance protein acrF - Synechocystis sp. (strain PCC 6803) | MYX12U_1681 | 3530 | Synechocystis sp. |
| hypothetical protein sll1053 - Synechocystis sp. (strain PCC 6803); acridine efflux pump | MYX12U_1682 | 3531 | Synechocystis sp. |
| acriflavin resistance protein acrF - Synechocystis sp. (strain PCC 6803) | MYX12U_1953 | 3802 | Synechocystis sp. |
| ragD protein - Bradyrhizobium japonicum; acridine efflux pump | MYX12U_1995 | 3844 | Bradyrhizobium japonicum |
| (AF188287) MtaD; gentamicin resistance protein | MYX12U_2103 | 3952 | Stigmatella aurantiaca |
| gentamicin resistance protein | MYX12U_2433 | 4282 | |
| macrolide 2'-phosphotransferase I; gentamicin resistance protein | MYX12U_2604 | 4453 | Escherichia coli |
| (AP001511) BH1390-unknown conserved protein in others; BICYCLOMYCIN RESISTANCE PROTEIN (bcr1) | MYX12U_2684 | 4533 | Bacillus halodurans |
| multidrug resistance protein D VCA0267 | MYX12U_2792 | 4641 | Vibrio cholerae |
| probable multidrug resistance protein VC0914 | MYX12U_2994 | 4843 | Vibrio cholerae |
| probable RND efflux membrane fusion protein precursor PA0156; acridine efflux pump | MYX12U_2995 | 4844 | Pseudomonas aeruginosa |
| excinuclease ABC chain A DRA0188; nogalamycin resistance protein snorO | MYX12U_3090 | 4939 | Deinococcus radiodurans |
| acridine efflux pump | MYX12U_3215 | 5064 | |
| (AB007646) UVB-resistance protein UVR8 | MYX12U_3288 | 5137 | Arabidopsis thaliana |
| (AB007646) UVB-resistance protein UVR8 | MYX12U_3518 | 5367 | Arabidopsis thaliana |

TABLE 4-continued

| GeneName | SEQ ID | SEQ NUM | Organism |
|---|---|---|---|
| probable RND efflux transporter PA2527; acriflavin resistance protein | MYX12U_3698 | 5547 | *Pseudomonas aeruginosa* |
| BICYCLOMYCIN RBSISTANCE PROTEIN (bcr1) | MYX12U_4106 | 5954 | |
| (AF097407) chloramphenicol and florfenicol resistance protein | MYX12U_4423 | 6271 | *Salmonella typhimurium* |
| (AF212366) spinster type I; chloramphenicol resistance protein | MYX12U_4610 | 6458 | *Drosophila melanogaster* |
| ACRIFLAVIN RESISTANCE PROTEIN A PRECURSOR | MYX12U_5142 | 6990 | *Escherichia coli* O157:H7 |
| RND multidrug efflux transporter MexD PA4598 | MYX12U_5143 | 6991 | *Pseudomonas aeruginosa* |
| chloramphenicol resistance protein homolog ybcL - *Bacillus subtilis* | MYX12U_5360 | 7208 | *Bacillus subtilis* |
| tetracycline-efflux transport - *Deinococcus radiodurans* (strain R1) | MYX12U_5499 | 7347 | *Deinococcus radiodurans* |
| beta-lactamase inhibitory protein II precursor | MYX12U_5989 | 7837 | *Streptomyces exfoliatus* |
| gentamicin resistance protein | MYX12U_5992 | 7840 | |
| EXCINUCLEASE ABC SUBUNIT A; nogalamycin resistance protein snorO | MYX12U_6339 | 8187 | *Thermus thermophilus* |
| EXCINUCLEASE ABC SUBUNIT A; nogalamycin resistance protein snorO | MYX12U_650 | 2499 | *Bacillus subtilis* |
| (AF146029) putative multidrug-resistance protein | MYX12U_6609 | 8457 | *Aeromonas hydrophila* |
| probable drug transport protein - *Deinococcus radiodurans* (strain R1) | MYX12U_6778 | 8626 | *Deinococcus radiodurans* |
| gentamicin resistance protein | MYX12U_6779 | 8627 | *Enterococcus gallinarum* |
| EXCINUCLEASE ABC SUBUNIT A; nogalamycin resistance protein snorO | MYX12U_7290 | 9138 | *Thermus thermophilus* |
| UVB-resistance protein UVR | MYX12U_867 | 2716 | |
| GENES ENCODING DNA MODIFICATION ENZYMES | | | |
| (AE005037) Vng1035c; EcoVIII modification methylase | MYX12U_1692 | 3541 | *Halobacterium* sp. NRC-1 |
| MODIFICATION METHYLASE AGEI (CYTOSINE-SPECIFIC METHYLTRANSFERASE AGEI) (M.AGEI) | MYX12U_207 | 2056 | *Ruegeria gelatinovora* |
| NAEI VERY-SHORT-PATCH-REPAIR ENDONUCLEASE (V.NAEI) | MYX12U_208 | 2057 | *Saccharothrix aerocolonigenes* |
| (BC001341) Unknown (protein for MGC:5621); endonuclease | MYX12U_7760 | 9608 | *Homo sapiens* |
| MODIFICATION METHYLASE LLADCHIB (ADENINE-SPECIFIC METHYLTRANSFERASE LLADCHIB) (M.LLADCHIB) (M.LLADCHI B) (M.LLAII B) | MYX12U_6856 | 8704 | *Lactococcus lactis* |
| methylase | MYX12U_7014 | 8862 | |
| SUCCINATE-SEMIALDEHYDE DEHYDROGENASE; endonuclease | MYX12U_6375 | 8223 | *Deinococcus radiodurans* |
| threonyl-tRNA synthetase NMB0720; endonuclease | MYX12U_6237 | 8085 | *Neisseria meningitidis* MC58 |
| (AF204951) EsV-1-164; methylase | MYX12U_5304 | 7152 | *Ectocarpus siliculosus* virus |
| (AL138977) putative DNA methylase. | MYX12U_475 | 2324 | *Streptomyces coelicolor* A3(2) |
| site-specific DNA-methyltransferase XF2313 | MYX12U_4885 | 6733 | *Xylella fastidiosa* |
| EcoVIII modification methylase | MYX12U_2131 | 3980 | |
| SIGMA FACTOR GENES | | | |
| RNA POLYMERASE SIGMA-B FACTOR | MYX12U_1226 | 3075 | *Stigmatella aurantiaca* |
| RNA POLYMERASE SIGMA FACTOR SIGZ | MYX12U_1453 | 3302 | *Bacillus subtilis* |
| probable RNA polymerase sigma factor - Streptomyces coelicolor | MYX12U_1962 | 3811 | *Streptomyces coelicolor* A3(2) |
| RNA POLYMERASE SIGMA FACTOR FOR FLAGELLAR OPERON (SIGMA-F FACTOR) (SIGMA-27) (SIGMA-28) | MYX12U_219 | 2068 | *Escherichia coli* O157:H7 |
| extracytoplasmic function alternative sigma factor | MYX12U_2210 | 4059 | *Mycobacterium avium* |
| (AF023662) sigma-D factor | MYX12U_247 | 2096 | *Myxococcus xanthus* |
| (AF023661) sigma-E factor | MYX12U_3542 | 5391 | *Myxococcus xanthus* |
| (AL589164) putative ECF sigma factor | MYX12U_3909 | 5757 | *Streptomyces coelicolor* |
| RNA polymerase sigma-E factor - *Thermotoga maritima* (strain MSB8) | MYX12U_4090 | 5938 | *Thermotoga maritima* |
| (AF190580) alternate sigma factor AlgT | MYX12U_4625 | 6473 | *Pseudomonas syringae* pv. syringae |
| (AL390188) putative ECF-sigma factor | MYX12U_523 | 2372 | *Streptomyces coelicolor* A3(2) |
| RNA POLYMERASE SIGMA-C FACTOR | MYX12U_5322 | 7170 | *Myxococcus xanthus* |
| (AF049107) putative ECF sigma factor RpoE1 | MYX12U_5673 | 7521 | *Myxococcus xanthus* |
| (AF023662) sigma-D factor | MYX12U_5880 | 7728 | *Myxococcus xanthus* |
| probable sigma factor - *Streptomyces coelicolor* | MYX12U_6110 | 7958 | *Streptomyces coelicolor* A3(2) |

TABLE 4-continued

| GeneName | SEQ ID | SEQ NUM | Organism |
|---|---|---|---|
| RNA polymerase sigma-E factor VC2467 | MYX12U_6142 | 7990 | Vibrio cholerae |
| RNA POLYMERASE SIGMA-C FACTOR | MYX12U_6425 | 8273 | Myxococcus xanthus |
| (AL391515) putative ECF-family RNA polymerase sigma factor | MYX12U_6450 | 8298 | Streptomyces coelicolor A3(2) |
| RNA POLYMERASE SIGMA FACTOR RPOD (SIGMA-80) | MYX12U_6510 | 8358 | Myxococcus xanthus |
| RNA POLYMERASE SIGMA FACTOR CARQ | MYX12U_6746 | 8594 | Myxococcus xanthus |
| probable sigma-70 factor, ECF subfamily PA2896 | MYX12U_6862 | 8710 | Pseudomonas aeruginosa |
| RNA polymerase sigma-H factor XF2239 | MYX12U_697 | 2546 | Xylella fastidiosa |
| (AP001507) RNA polymerase ECF-type sigma factor | MYX12U_7164 | 9012 | Bacillus halodurans |
| RNA polymerase sigma-E factor VC2467 | MYX12U_7301 | 9149 | Vibrio cholerae |
| probable sigma factor - Mycobacterium tuberculosis (strain H37RV) | MYX12U_7558 | 9406 | Mycobacterium tuberculosis |
| extracytoplasmic function alternative sigma factor | MYX12U_759 | 2608 | Mycobacterium avium |
| sigma32-like factor RpoH1 | MYX12U_7661 | 9509 | Bradyrhizobium japonicum |
| RNA polymerase ECF-type sigma factor (sigma-Y) | MYX12U_2854 | 4703 | |
| RNA polymerase sigma-E factor | MYX12U_2934 | 4783 | |
| RNA polymerase ECF-type sigma factor (sigma-Z) | MYX12U_3078 | 4927 | |
| RNA POLYMERASE SIGMA FACTOR CARQ | MYX12U_3164 | 5013 | |
| Sigma D factor | MYX12U_3715 | 5564 | |
| Sigma D factor | MYX12U_6271 | 8119 | |
| (AL132973) hypothetical protein SCF91.02c; Sigma D factor | MYX12U_7245 | 9093 | Streptomyces coelicolor A3(2) |
| RNA polymerase ECF-type sigma factor (sigma-W) | MYX12U_3817 | 5665 | |
| RNA polymerase ECF-type sigma factor (sigma-W) | MYX12U_6753 | 8601 | |
| Sigma factor | MYX12U_6138 | 7986 | |
| GTP-binding protein HflX - Deinococcus radiodurans (strain R1); sigma factor | MYX12U_7461 | 9309 | Deinococcus radiodurans |
| NITRATE PATHWAY ENZYMES AND REGULATORY GENES | | | |
| small subunit of cytochrome c nitrite reductase | MYX12U_1126 | 2975 | |
| transport protein MsbA PA4997; ABC transporter, ATP-binding protein | MYX12U_1139 | 2988 | Pseudomonas aeruginosa |
| (AF273214) SasR; response regulator of the NtrC family | MYX12U_1270 | 3119 | Myxococcus xanthus |
| frdD homolog socA2 - Myxococcus xanthus; quarternary ammonium determinant | MYX12U_142 | 1991 | |
| (AG273214) SasR: sigma-54 dependent transcriptional activator | MYX12U_1421 | 3270 | Myxococcus xanthus |
| probable formate hydrogenlyase transcription activator (fh1A) - syphilis spirochete; sigma-54 dependent transcriptional activator | MYX12U_1486 | 3335 | Treponema pallidum |
| putative sigma-54 dependent transcriptional activator | MYX12U_1620 | 3469 | Myxococcus xanthus |
| probable phosphoesterase (EC 3.1.-.-) yvnB - Bacillus subtilis; nitrate reductase (NADH) | MYX12U_1821 | 3670 | Bacillus subtilis |
| small subunit of cytochrome c nitrite reductase | MYX12U_1848 | 3697 | |
| probable two-component response regulator PA4726; sigma-54 dependent transcriptional activator | MYX12U_1882 | 3731 | Pseudomonas aeruginosa |
| (AY013246) putative ABC transporter | MYX12U_2224 | 4073 | Hordeum vulgare |
| (AE005611) putative arylsulfatase regulator; heme biosynthesis protein (nirJ-2) | MYX12U_2233 | 4082 | Escherichia coli O157:H7 |
| (AL353832) molecular chaperone; quarternary ammonium determinant | MYX12U_233 | 2082 | Streptomyces coelicolor A3(2) |
| ATP-binding cassette, sub-family B, member 12; Abc-mitochondrial erythroid | MYX12U_2362 | 4211 | Mus musculus |
| probable periplasmic cytochrome C Cj1357c nitrite reductase | MYX12U_2790 | 4639 | Campylobacter jejuni |
| (AJ245540) small subunit of cytochrome c nitrite reductase | MYX12U_2791 | 4640 | Wolinella succinogenes |
| (AJ223604) gacE2, quarternary ammonium determinant | MYX12U_294 | 2143 | Pseudomonas aeruginosa |
| (AL353832) molecular chaperone; quarternary ammonium determinant | MYX12U_6026 | 7874 | Streptomyces coelicolor A3(2) |
| (AF205943) quaternary ammonium compound resistance protein | MYX12U_949 | 2798 | Escherichia coli |
| NrpB; ABC transporter, ATP-binding protein | MYX12U_3072 | 4921 | Proteus mirabilis |
| heme biosynthesis protein (nirJ-2) | MYX12U_6232 | 8080 | Pseudomonas putida |

TABLE 4-continued

| GeneName | SEQ ID | SEQ NUM | Organism |
|---|---|---|---|
| probable pqqE protein - *Mycobacterium tuberculosis* (strain H37RV); heme biosynthesis protein (nirJ-2) | MYX12U_3100 | 4949 | *Mycobacterium tuberculosis* |
| molybdopterin biosynthetic protein A1 PA3870; heme biosynthesis protein (nirJ-2) | MYX12U_5060 | 6908 | *Pseudomonas aeruginosa* |
| ORF393 protein; heme biosynthesis protein (nirJ-2) | MYX12U_1954 | 3803 | *Pseudomonas stutzeri* |
| formate dehydrogenase homolog yrhE - *Bacillus subtilis* | MYX12U_348 | 2197 | *Bacillus subtilis* |
| DMSO reductase chain A - *Aquifex aeolicus* | MYX12U_4661 | 6509 | *Aquifex aeolicus* |
| probable formate dehydrogenase - *Streptomyces coelicolor* | MYX12U_5029 | 6877 | *Streptomyces coelicolor* A3(2) |
| probable oxidoreductase PA3534 | MYX12U_7098 | 8946 | *Pseudomonas aeruginosa* |
| ADENYLATE CYCLASE 2 (ATP PYROPHOSPHATE-LYASE 2) (ADENYLYL CYCLASE 2) (AC2); small subunit of cytochrome c nitrite reductase | MYX12U_3654 | 5503 | *Stigmatella aurantiaca* |
| ACETOACETATE METABOLISM REGULATORY PROTEIN ATOC (ORNITHINE/ARGININE DECARBOXYLASE INHIBITOR) (ORNITHINE DECARBOXYLASE ANTIZYME); sigma-54 dependent transcriptional activator | MYX12U_3816 | 5664 | *Escherichia coli* K12 |
| regulator protein pilR - *Myxococcus xanthus*; sigma-54 dependent transcriptional activator | MYX12U_5547 | 7395 | *Myxococcus xanthus* |
| sodium ABC transporter ATP-binding protein XF2329 | MYX12U_3898 | 5746 | *Xylella fastidiosa* |
| probable ABC transporter ATP-binding protein APE2579 - *Aeropyrum pernix* (strain K1) | MYX12U_6313 | 8161 | *Aeropyrum pernix* |
| HYPOTHETICAL 52.8 KD PROTEIN SLR0074; ABC transporter ATP-binding protein | MYX12U_6731 | 8579 | *Synechocystis* sp. |
| glutamine ABC transporter, ATP-binding protein (glnQ) | MYX12U_7636 | 9484 | *Archaeoglobus fulgidus* |
| probable ferredoxin reductase PA4331; nitrate reductase (NADH) | MYX12U_3929 | 5777 | *Pseudomonas aeruginosa* |
| short-chain alcohol dehydrogenase homolog socA1 - *Myxococcus xanthus*; nitrate reductase (NADH) | MYX12U_4384 | 6232 | |
| hypothetical protein Rv3230c - *Mycobacterium tuberculosis* (strain H37RV); nitrate reductase (NADH) | MYX12U_6620 | 8468 | *Mycobacterium tuberculosis* |
| probable esterase/lipase - *Streptomyces coelicolor*; nitrate reductase (NADH) | MYX12U_72 | 1921 | *Streptomyces coelicolor* A3(2) |
| catalytic subunit of cytochrome c nitrite reductase | MYX12U_3952 | 5800 | |
| catalytic subunit of cytochrome c nitrite reductase | MYX12U_4144 | 5992 | |
| catalytic subunit of cytochrome c nitrite reductase | MYX12U_4550 | 6398 | |
| catalytic subunit of cytochrome c nitrite reductase | MYX12U_6724 | 8572 | |
| COLICIN I RECEPTOR PRECURSOR; RNA polymerase sigma-54 factor | MYX12U_3964 | 5812 | *Escherichia coli* |
| hypothetical protein PA0830; RNA polymerase sigma-54 factor | MYX12U_5307 | 7155 | *Pseudomonas aeruginosa* |
| RNA polymerase sigma-54 factor | MYX12U_5344 | 7192 | *Myxococcus xanthus* |
| ATP-DEPENDENT PROTEASE LA 1; RNA polymerase sigma-54 factor | MYX12U_6280 | 8128 | *Myxococcus xanthus* |
| (AL353861) hypothetical protein; RNA polymerase sigma-54 factor | MYX12U_6691 | 8539 | *Streptomyces coelicolor* A3(2) |
| (AF305914) HydG, response regulator of the NtrC family | MYX12U_5069 | 6917 | *Klebsiella oxytoca* |
| probable response regulatory protein (atoC) - *syphilis spirochete*; response regulator of the NtrC family | MYX12U_6204 | 8052 | *Treponema pallidum* |
| (AF305914) HydG; response regulator of the NtrC family | MYX12U_7272 | 9120 | *Klebsiella oxytoca* |
| (AF273214) SasR; sigma-54 dependent transcriptional activator | MYX12U_5333 | 7181 | *Myxococcus xanthus* |
| (AF170176) *Salmonella typhimurium* transcriptional regulatory protein (HYDG) (SW:P25852); contains similarity to Pfam domain PF00158 (sigma54), Score = 609.2, E = 2.4e-179, N = 1 and PF00072 (response_reg), Score = 158, E = 1.6e-43, N = 1 [*Salmonella* | MYX12U_6325 | 8173 | *Salmonella typhimurium* LT> [ |

TABLE 4-continued

| GeneName | SEQ ID | SEQ NUM | Organism |
|---|---|---|---|
| *typhimurium* LT>; sigma-54 dependent transcriptional activator | | | |
| probable response regulatory protein (atoC) - *syphilis spirochete*; NtrC/NifA4-like protein regulator | MYX12U_5532 | 7380 | *Treponema pallidum* |
| NtrC/NifA-like protein regulator | MYX12U_6285 | 8133 | |
| (AF204400) FrgC; NtrC/NifA-like protein regulator | MYX12U_7311 | 9159 | *Myxococcus xanthus* |
| (AF204400) FrgC; NtrC/NifA-like protein regulator | MYX12U_3361 | 5210 | *Myxococcus xanthus* |
| (AF163841) putative response regulator; NtrC/NifA-like protein regulator | MYX12U_19 | 1868 | *Myxococcus xanthus* |
| ACETOACETATE METABOLISM REGULATORY PROTEIN ATOC (ORNITHINE/ARGININE DECARBOXYLASE INHIBITOR) (ORNITHINE DECARBOXYLASE ANTIZYME); nitrogen regulation | MYX12U_5690 | 7538 | *Escherichia coli* K12 |
| putative sigma-54 dependent transcriptional activator | MYX12U_5871 | 7719 | *Myxococcus xanthus* |
| probable two-component response regulator PA4726; nitrogen regulation | MYX12U_7707 | 9555 | *Pseudomonas aeruginosa* |
| (AF273214) SasR; sigma-54 dependent transcriptional activator | MYX12U_6056 | 7904 | *Myxococcus xanthus* |
| ACETOACETATE METABOLISM REGULATORY PROTEIN ATOC (ORNITHINE/ARGININE DECARBOXYLASE INHIBITOR)(ORNITHINE DECARBOXYLASE ANTIZYME); sigma-54 dependent transcriptional activator | MYX12U_6103 | 7951 | *Escherichia coli* K12 |
| (AF273214) SasR; sigma-54 dependent transcriptional activator | MYX12U_6776 | 8624 | *Myxococcus xanthus* |
| (AF305914) HydG; sigma-54 dependent transcriptional activator | MYX12U_7061 | 8909 | *Klebsiella oxytoca* |
| ACETOIN CATABOLISM REGULATORY PROTEIN; sigma-54 dependent transcriptional activator | MYX12U_7337 | 9185 | *Ralstonia eutropha* |
| (AE002331) ABC transporter, ATP-binding protein | MYX12U_6558 | 8406 | *Chlamydia muridarum* |
| putative sigma-54 dependent transcriptional activator | MYX12U_2120 | 3969 | *Myxococcus xanthus* |
| regulator protein pi1R - *Myxococcus xanthus*; sigma-54 dependent transcriptional activator | MYX12U_7240 | 9088 | *Myxococcus xanthus* |
| (AF047554) putative ABC transporter | MYX12U_7747 | 9595 | *Myxococcus xanthus* |
| (AF026065) positive phenol-degradative gene regulator; PoxR; putative sigma-54 dependent transcriptional activator | MYX12U_3535 | 5384 | *Ralstonia* sp. E2 |
| regulator protein pi1R - *Myxococcus xanthus*; putative sigma-54 dependent transcriptional activator | MYX12U_4901 | 6749 | *Myxococcus xanthus* |
| (AP273214) SasR; putative sigma-54 dependent transcriptional activator | MYX12U_6635 | 8483 | *Myxococcus xanthus* |

All publications and patent applications are herein incorporated by reference in their entirely to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6833447B1). An electronic copy of the "Sequence Listing" will also be available from the USPTO upon request and payment of the fee set forth in 37 CFR 1.19(b)(3).

We claim:

1. A substantially purified nucleic acid molecule encoding a nitrite reductase of SEQ ID NO:11926.

2. A recombinant DNA construct for expression of a nitrite reductase gene in a plant cell, wherein said construct comprises a promoter functional in a plant cell operatively linked to a nucleic acid molecule encoding a nitrite reductase protein of at least 70 percent sequence identity to SEQ ID NO:11926 over the entire length of said protein.

3. The recombinant DNA construct of claim 2, wherein said nucleic acid molecule encodes a nitrite reductase protein of at least 90 percent sequence identity to SEQ ID NO:11926 over the entire length of said protein.

4. The recombinant DNA construct of claim 2, wherein said nucleic acid molecule encodes a nitrite reductase of SEQ ID NO:11926.

5. A plant cell comprising a recombinant DNA construct of claim 2.

* * * * *